(12) United States Patent
Furusawa et al.

(10) Patent No.: US 8,536,861 B2
(45) Date of Patent: Sep. 17, 2013

(54) WIRE ROPE FLAW DETECTOR

(75) Inventors: Kimiyasu Furusawa, Chiyoda-ku (JP);
Taizo Iwami, Chiyoda-ku (JP); Takashi Yoshioka, Chiyoda-ku (JP); Hiroshi Sasai, Chiyoda-ku (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 368 days.

(21) Appl. No.: 12/525,175

(22) PCT Filed: Jan. 31, 2007

(86) PCT No.: PCT/JP2007/051562
§ 371 (c)(1),
(2), (4) Date: Sep. 14, 2009

(87) PCT Pub. No.: WO2008/093410
PCT Pub. Date: Aug. 7, 2008

(65) Prior Publication Data
US 2010/0019762 A1    Jan. 28, 2010

(51) Int. Cl.
*G01N 27/83* (2006.01)

(52) U.S. Cl.
USPC ........................... 324/240; 324/241; 324/242

(58) Field of Classification Search
USPC ....................................................... 324/240
See application file for complete search history.

(56) References Cited

U.S. PATENT DOCUMENTS

| | | | |
|---|---|---|---|
| 4,096,437 A | | 6/1978 | Kitzinger et al. |
| 4,427,940 A | * | 1/1984 | Hirama et al. ............... 324/240 |
| 4,659,991 A | * | 4/1987 | Weischedel .................. 324/241 |
| 5,565,771 A | | 10/1996 | Hamelin |
| 5,804,964 A | * | 9/1998 | Hamelin et al. .............. 324/242 |
| 2007/0090834 A1 | * | 4/2007 | Osada et al. .................. 324/240 |

FOREIGN PATENT DOCUMENTS

| | | | |
|---|---|---|---|
| EP | 1676806 A1 | * | 7/2006 |
| JP | 56-044840 A | | 4/1981 |
| JP | 02-257055 | | 10/1990 |
| JP | 6-87861 U | | 12/1994 |
| JP | 9-210968 A | | 8/1997 |
| JP | 2005-089172 A | | 4/2005 |

OTHER PUBLICATIONS

Office Action (First Notice of Reasons for Rejection) dated Jul. 7, 2011, issued in the corresponding Chinese Patent Application No. 200780050683.X, and an English Translation thereof.

(Continued)

*Primary Examiner* — Arleen M Vazquez
*Assistant Examiner* — Son Le
(74) *Attorney, Agent, or Firm* — Buchanan Ingersoll & Rooney PC

(57) ABSTRACT

A wire rope flaw detector includes a magnetizer having a pair of exciting magnets disposed on a back yoke such that polarities thereof are opposite to each other, and forming a main magnetic path in a predetermined segment in an axial direction of a wire rope; and a leakage magnetic flux detection section disposed in the predetermined segment in the axial direction, and detecting leakage magnetic flux generated from a damaged portion of the wire rope. Each of the exciting magnets are formed so as to have a cross-section of a shape that embraces the wire rope when each exciting magnet is cut along a plane perpendicular to the axial direction of the wire rope, and has magnetic orientation, on the cross-section of the exciting magnet, oriented from at least two directions toward the wire rope.

4 Claims, 27 Drawing Sheets

(56) References Cited

OTHER PUBLICATIONS

Office Action dated May 16, 2011, issued in the corresponding Korean Patent Application No. 10-2009-7016103.
Office Action from German Patent Office issued in corresponding German Patent Application No. 11 2007 003 313.4-52 dated Dec. 23, 2010, and an English translation thereof.
Form PCT/ISA/210 (International Search Report) dated Apr. 17, 2007.
Office Action dated Jun. 1, 2012 issued in a corresponding Chinese application, with English language translation, 13 pps.
Second Notice of Reason for Rejection in Corresponding Chinese Patent Application No. 200780050683 dated Feb. 6, 2012, and an English-language translation, 8 pps.

* cited by examiner (a) COMPARATIVE EXAMPLE (b) EMBODIMENT 1

(a) COMPARATIVE EXAMPLE (b) EMBODIMENT 1

WIRE ROPE FLAW DETECTOR

TECHNICAL FIELD

The present invention relates to a wire rope flaw detector for detecting any damage in a wire rope and disconnection of a component wire thereof (hereinafter collectively referred to as a damaged portion of the wire rope), the wire rope suspending a car of an elevator or the like.

BACKGROUND ART

Conventionally disclosed is a wire rope flaw detector which uses a detection coil to detect leakage magnetic flux generated from a damaged portion, such as a disconnection of a component wire, of a wire rope in a magnetic saturated state, whereby the damaged portion of the wire rope is detected (e.g., see patent document 1).
[Patent document 1] Japanese Laid-Open Patent Publication No. H09-210968 (Paragraph [0003], FIG. 8, and the like)

DISCLOSURE OF THE INVENTION

Problems to be Solved by the Invention

The above conventional wire rope flaw detector exerts sufficient detection performance with respect to damage on a surface and its vicinity of a wire rope, but has a problem of failing to detect damage located inside the wire rope. For example, as described in patent document 1, in a method of detecting local leakage magnetic flux in the vicinity of the damaged portion of the wire rope, an induced electromotive force generated in the detection coil is proportional to an amount of the leakage magnetic flux. Therefore, in order to increase detection sensitivity, the leakage magnetic flux in the vicinity of the damaged portion needs to be increased by applying a larger amount of magnetic flux to the damaged portion and its vicinity of the wire rope.

However, the more an air gap between the wire rope and an exciting permanent magnet is increased, the smaller the amount of the magnetic flux flowing through the wire rope becomes. Accordingly, at a position distant from the surface of the wire rope toward the inside, a smaller amount of the magnetic flux flows. Therefore, in the case where a damaged portion is located inside the wire rope, sufficient leakage magnetic flux cannot be obtained, and the induced electromotive force generated in the detection coil is decreased, which leads to a problem of deterioration in the detection sensitivity. In order to solve such a problem, patent document 1 has a configuration in which a magnetic pole piece having low magnetic reluctance is disposed at a portion of an air gap, the portion having high magnetic reluctance, such that a larger amount of magnetic flux flows through the wire rope. However, as shown in FIG. 32, magnetic flux (MG1) generated from a permanent magnet 500 is divided into magnetic flux (MG2) that flows into the wire rope 1 passing through a magnetic pole piece 400 and leakage magnetic flux (MG3) that returns to the permanent magnet 500 without flowing into the wire rope 1. That is, there has been a problem that the magnetic flux generated from the permanent magnet 500 cannot be caused to efficiently flow into the wire rope 1.

The present invention is invented to solve the above problems, and is directed to a wire rope flaw detector with high detection sensitivity, which minimizes leakage of magnetic flux generated from a permanent magnet so as to allow a larger amount of magnetic flux to flow into the wire rope, thereby obtaining a sufficient amount of leakage magnetic flux even if a damaged portion is located inside the wire rope.

Solution to the Problems

The wire rope flaw detector according to the present invention includes: a magnetizer including a back yoke, and a pair of exciting magnets disposed on the back yoke such that polarities thereof are opposite to each other, and forming a main magnetic path in a predetermined segment in an axial direction of a wire rope; and a leakage magnetic flux detection section disposed in the predetermined segment in the axial direction of the wire rope, and detecting leakage magnetic flux generated from a damaged portion of the wire rope. Each of the exciting magnets has a cross-section of a shape that embraces the wire rope when the exciting magnet is cut along a plane perpendicular to the axial direction of the wire rope, and has a magnetic orientation, on the cross-section, oriented from at least two directions toward the wire rope.

Effect of the Invention

According to a wire rope flaw detector of the present invention, exciting magnets used therein each has a cross-section of a shape that embraces a wire rope when cut along a plane perpendicular to an axial direction of the wire rope, and has a magnetic orientation on the cross-section of the wire rope oriented from at least two directions toward the wire rope, whereby magnetic flux leaking outside the wire rope without flowing thereinto is reduced, and a larger amount of magnetic flux is allowed to flow into the wire rope. Therefore, regardless of the position of a damaged portion in the wire rope, it is possible to obtain a sufficiently large amount of leakage magnetic flux, and accordingly, it is possible to obtain a signal having an SN ratio sufficient to detect the damaged portion with the use of the leakage magnetic flux detection section.

BRIEF DESCRIPTION OF THE DRAWINGS

FIG. 25 is a cross-sectional view of the exciting permanent magnet shown in FIG. 24 as cut along a plane perpendicular to a direction in which the wire rope is running through.

FIG. 26 is a cross-sectional view of another exemplary exciting permanent magnet, according to embodiment 2 of the present invention, as cut along a plane perpendicular to the direction in which the wire rope is running through.

BEST MODE FOR CARRYING OUT THE INVENTION

Hereinafter, preferred embodiments for carrying out the present invention will be described with reference to drawings.

Embodiment 1

Figure 1:
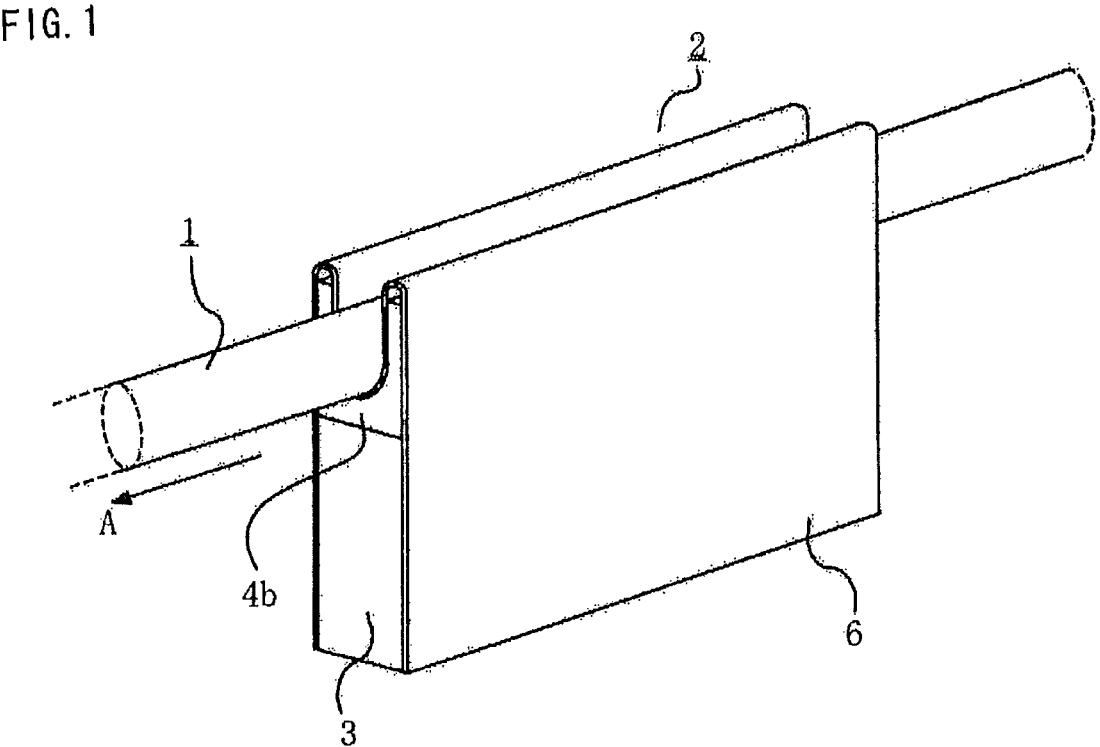
FIG. 1 is a perspective view showing a wire rope flaw detector according to embodiment 1 of the present invention.

FIG. 1 is a perspective view showing a wire rope flaw detector according to embodiment 1 of the present invention. In FIG. 1, a wire rope flaw detector 2 has a guide plate 6 having a guiding groove 6a of an approximate U-shape so as to allow a wire rope 1 to run therethrough (as indicated by A in the drawing). The wire rope flaw detector 2 includes a magnetizer forming a main magnetic path in a predetermined segment along an axial direction of the wire rope 1, and a leakage magnetic flux detection section detecting leakage magnetic flux generated from a damaged portion of the wire rope 1.

Figure 2:
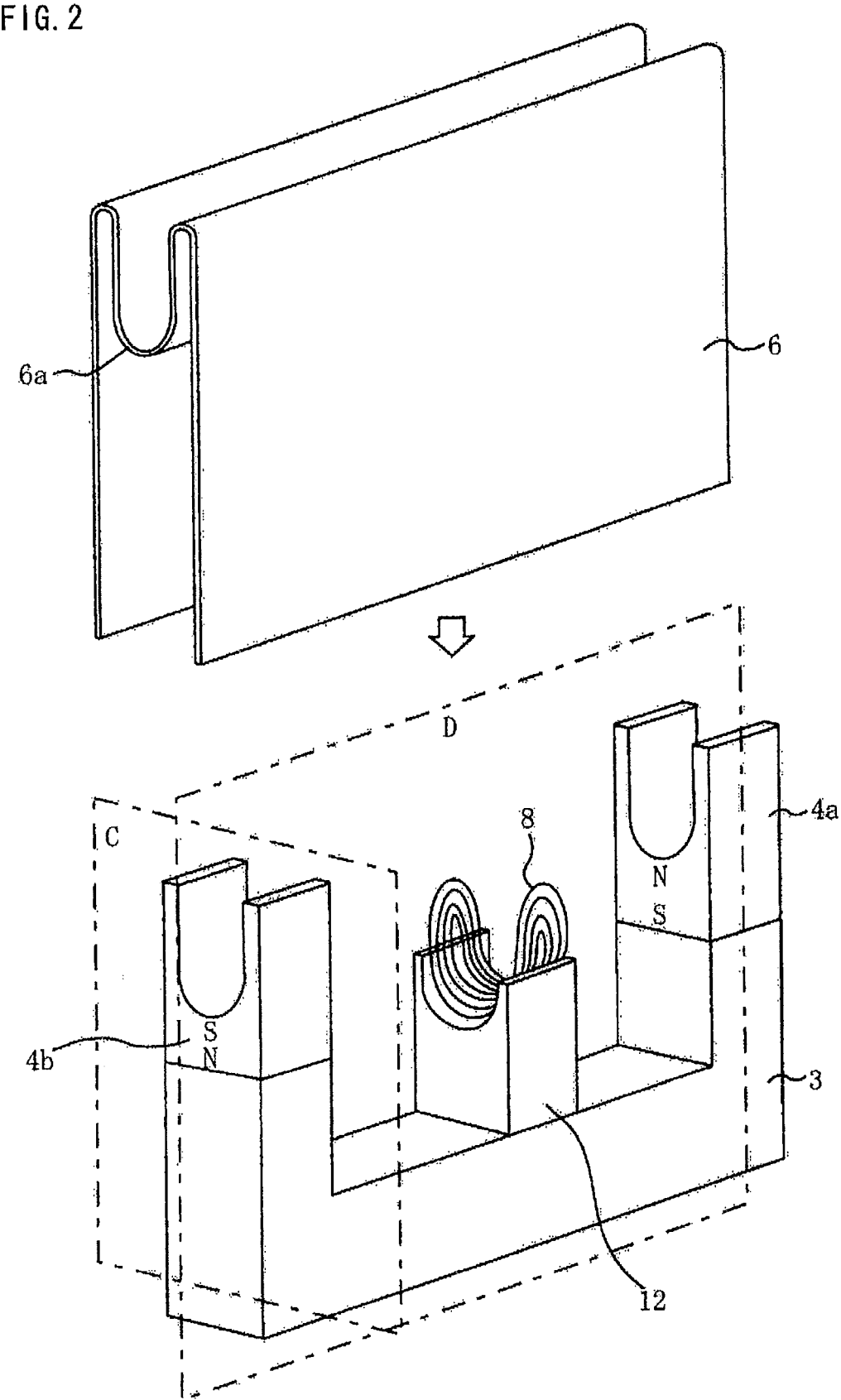
FIG. 2 is a perspective view showing an appearance of the wire rope flaw detector shown in FIG. 1, in a state where a guide plate thereof is removed.

FIG. 2 is a perspective view showing an appearance of the wire rope flaw detector shown in FIG. 1, in a state where the guide plate is removed. The magnetizer included in the wire rope flaw detector 2 is designed to form the main magnetic path in a predetermined segment along the axial direction of the wire rope 1, and includes a back yoke 3 made of a ferromagnetic material such as iron or the like, and a pair of exciting permanent magnets 4a and 4b, which are bonded, with an acrylic or epoxide-based adhesive, on both ends of the back yoke 3 so as to be distant from each other by a predetermined distance (about 100 mm), and disposed such that polarities thereof are opposite to each other.

The leakage magnetic flux detection section included in the wire rope flaw detector 2 has a base 12 which is made of non-magnetic material such as aluminum, stainless steel, or the like, is disposed between the pair of permanent magnets 4a and 4b, and is fixed onto the back yoke 3; and a detection coil 8 which is disposed between the guide plate 6 and the base 12, and is made by winding a copper wire having a diameter of 0.05 mm, for example, by 500 turns. The detection coil 8 has a cross-section of a U-shape, when cut along a plane perpendicular to a direction in which the wire rope 1 runs, so as to embrace the wire rope 1. In this case, it is preferable that a height of the detection coil 8 is greater than an outer diameter of the wire rope 1 so that a largest possible amount of leakage magnetic flux is linked with the detection coil 8 and consequently induced electromotive force is increased even if the damaged portion 10 is located at lateral surfaces of the wire rope.

The guide plate 6 is made of a non-magnetic material such as stainless steel or the like, formed by bending a band plate so as to substantially adhere to a U-shaped groove of each of the exciting permanent magnets 4a and 4b, and screwed onto side surfaces of the back yoke 3. The guide plate 6 has a function of protecting the detection coil 8, and also has a guiding function of allowing the wire rope 1 to run smoothly.

Figure 3:
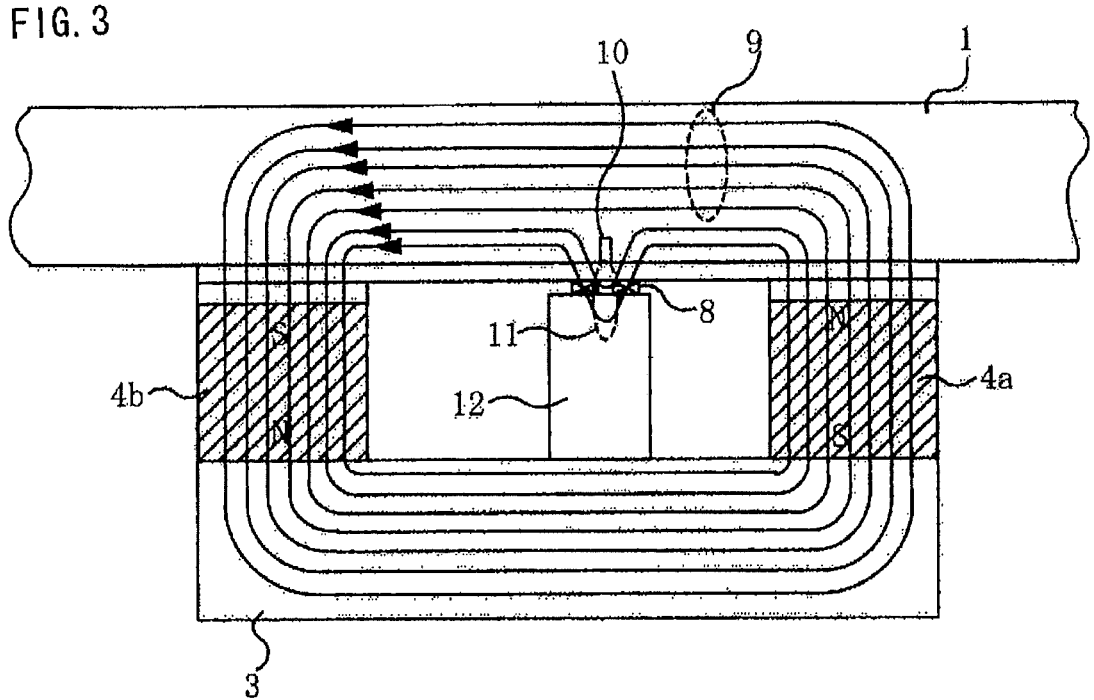
FIG. 3 is a cross-sectional view of the wire rope flaw detector according to embodiment 1 of the present invention and a wire rope as cut along a plane parallel to an axial direction of the wire rope.

FIG. 3 is a cross-sectional view of the wire rope and the wire rope flaw detector as cut along a plane D which is parallel to the axial direction of the wire rope 1 shown in FIG. 2, and shows a flow of the magnetic flux when the damaged portion 10 of the wire rope passes near the detection coil 8. Main magnetic flux 9 generated from the permanent magnet 4a passes through the wire rope 1, the permanent magnet 4b, and back yoke 3, and then returns to the permanent magnet 4a. When the damaged portion 10 of the wire rope 1 passes near the detection coil 8, local leakage magnetic flux 11 generated in the vicinity of the damaged portion 10 is linked with the detection coil 8, and thus an induced electromotive force is generated in the detection coil 8, whereby a position of the damaged portion 10 can be detected.

Figure 4:
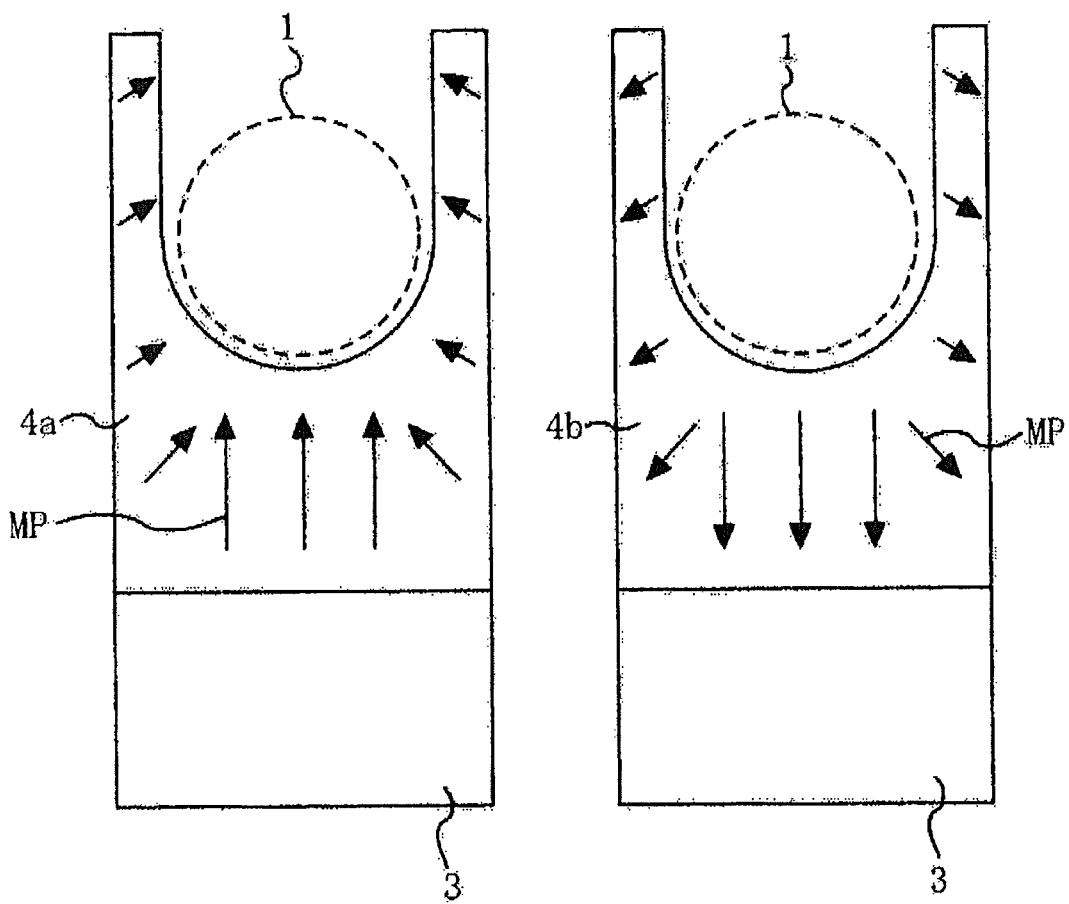
FIG. 4 is a cross-sectional view of exciting magnets included in the wire rope flaw detector according to embodiment 1 of the present invention as cut along a plane perpendicular to the axial direction of the wire rope.

FIG. 4 is a cross-sectional view of the exciting permanent magnet as cut along a plane C perpendicular to the axial direction of the wire rope 1 shown in FIG. 2. As shown in FIG. 4, a magnetic orientation MP of each of the exciting permanent magnets 4a and 4b is oriented toward the wire rope 1. The cross-section of each of the exciting permanent magnets 4a and 4b, as cut along a plane perpendicular to the axial direction of the wire rope 1, is of a U-shape which includes an arc shape portion having a curvature radius of 6.25 mm, and which is able to embrace the wire rope 1 having a cross-sectional radius of 6 mm. The wider an air gap between the wire rope 1 and the exciting permanent magnets 4a and 4b is, the more the magnetic flux flowing into the wire rope 1 decreases. Therefore, the curvature of the arc of the U-shaped cross-section of each of the exciting permanent magnets 4a and 4b is set to accommodate only the radius of the cross-section of the wire rope as well as a thickness of the guide plate 6, whereby the air gap is preferably set as small as possible. Further, in order to reduce an amount of leakage of the magnetic flux that does not flow into the wire rope 1, a depth of the groove of each of the exciting permanent magnets 4a and 4b, the groove having a U-shaped cross-section, is preferably formed so as to be greater than the height of the wire rope 1.

Figure 5:
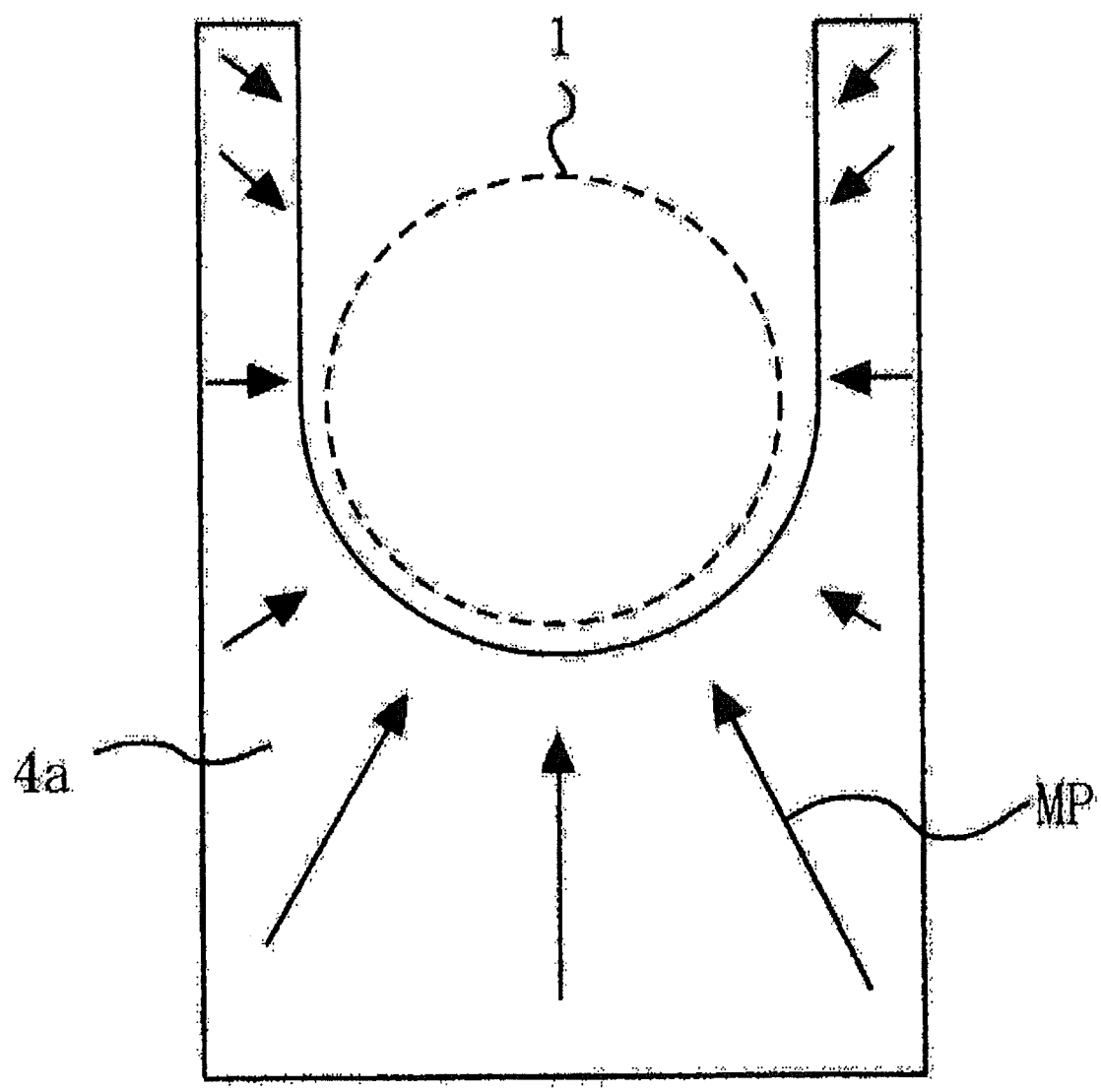
FIG. 5 is a cross-sectional view of the exciting magnets included in the wire rope flaw detector according to embodiment 1 of the present invention as cut along a plane perpendicular to the axial direction of the wire rope.

Further, as shown in FIG. 5, when the magnetic orientation MP of each of the exciting permanent magnets 4a and 4b is oriented toward a central axis of the wire rope 1, the leakage of the magnetic flux that does not flow into the wire rope 1 can be reduced to a lesser degree, which is further preferable. With this configuration, it is possible to cause a larger amount of magnetic flux to flow into the wire rope 1, and consequently it is possible to increase the local leakage magnetic flux 11.

Figure 6:
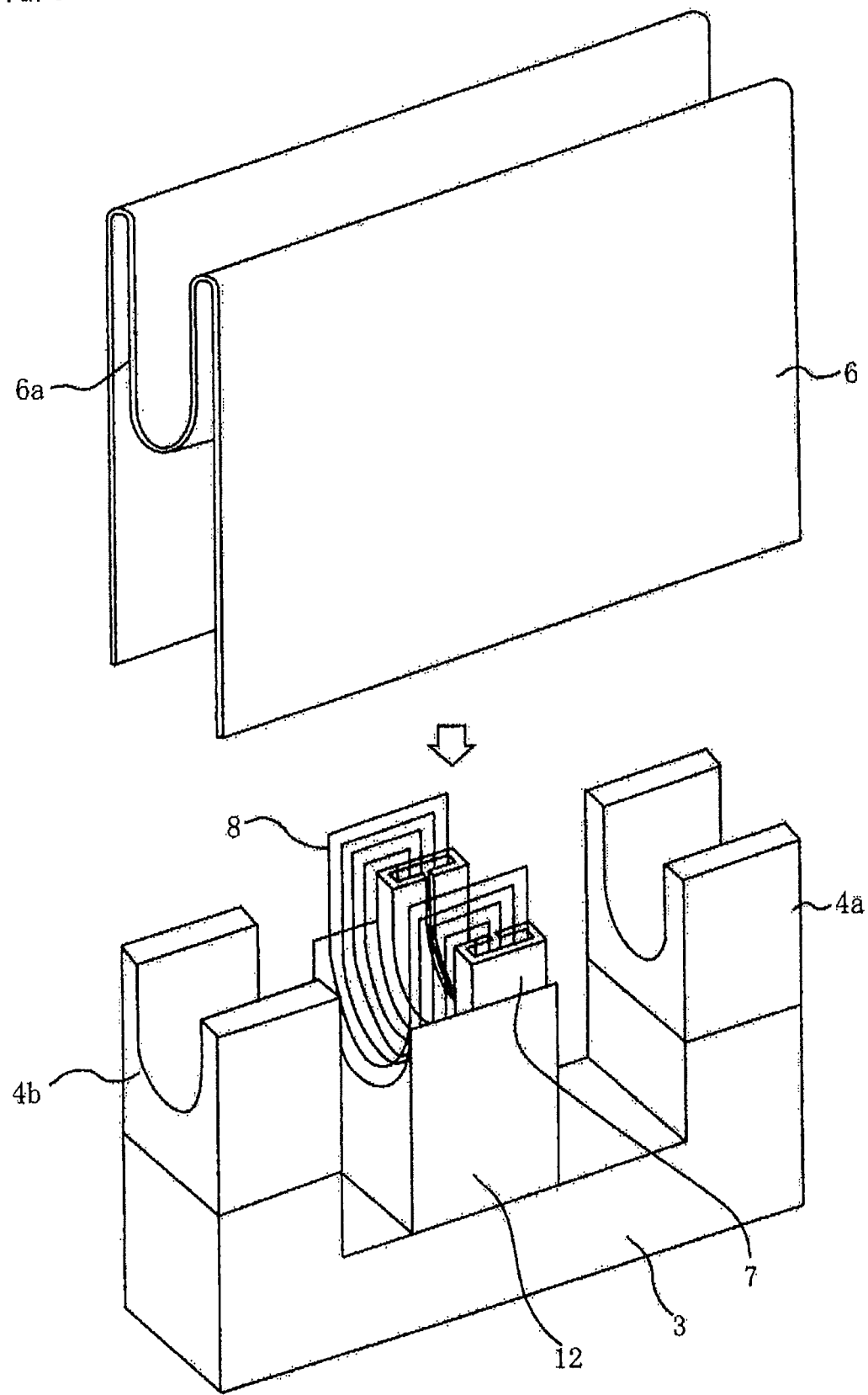
FIG. 6 is a perspective view showing another wire rope flaw detector according to embodiment 1 of the present invention.
Figure 7:
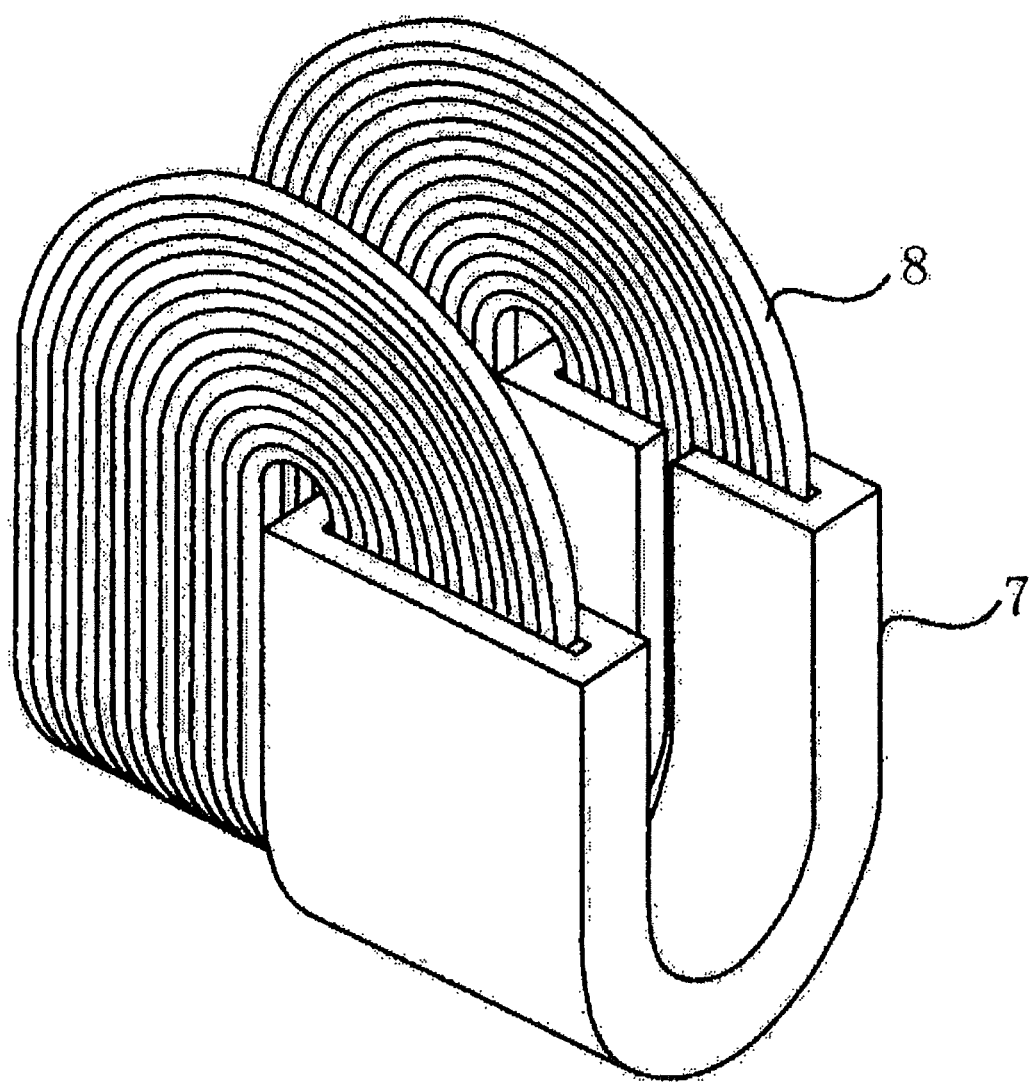
FIG. 7 is a perspective view showing a magnetic path member of the wire rope flaw detector shown in FIG. 6.

FIG. 6 is a perspective view showing another wire rope flaw detector according to embodiment 1 of the present invention, and FIG. 7 is a perspective view showing a magnetic path member of the wire rope flaw detector shown in FIG. 6. The wire rope flaw detector shown in FIG. 6 has a magnetizer which includes a back yoke 3 and a pair of exciting magnets disposed on both ends of the back yoke 3 such that polarities thereof are opposite to each other and which forms a main magnetic path in a predetermined segment along an axial direction of a wire rope, a magnetic path member 7 which is disposed in the predetermined segment so as to be magnetically insulated from the magnetizer and which causes leakage magnetic flux 11 generated from the damaged portion 10 of the wire rope to detour around the wire rope, and a detection coil 8 which is wound around the magnetic path member 7 so as to detect the leakage magnetic flux. The magnetic path member 7 has a cross-section of an approximate U-shape or of an approximate C-shape when the magnetic path member is cut along a plane including the central axis of the wire rope 1, and is situated such that an opening portion of the cross-section faces the wire rope 1. Further the magnetic path member 7 is disposed so as to surround the outer circumference of the wire rope 1, and has a cross-section of an approximate U-shape when the magnetic path member 7 is cut along a plane perpendicular to the central axis of the wire rope 1. The detection coil 8 to detect the leakage magnetic flux is wound around the magnetic path member 7.

Figure 8:
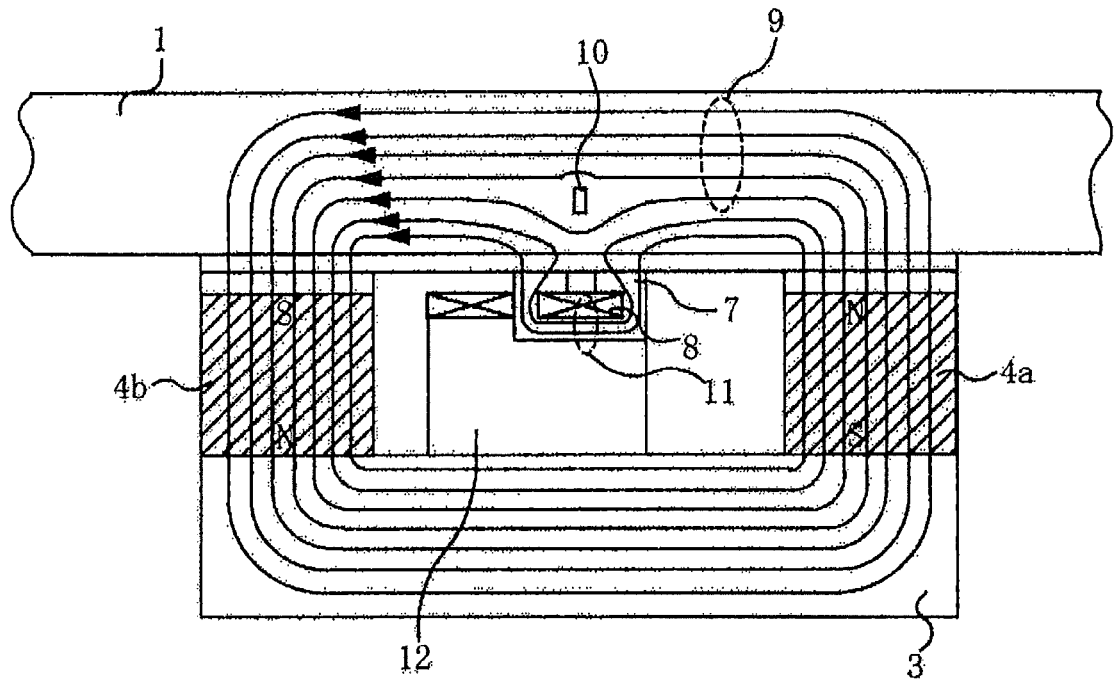
FIG. 8 is a cross-sectional schematic view of a wire rope flaw detector with the magnetic path member shown in FIG. 6.
Figure 9:
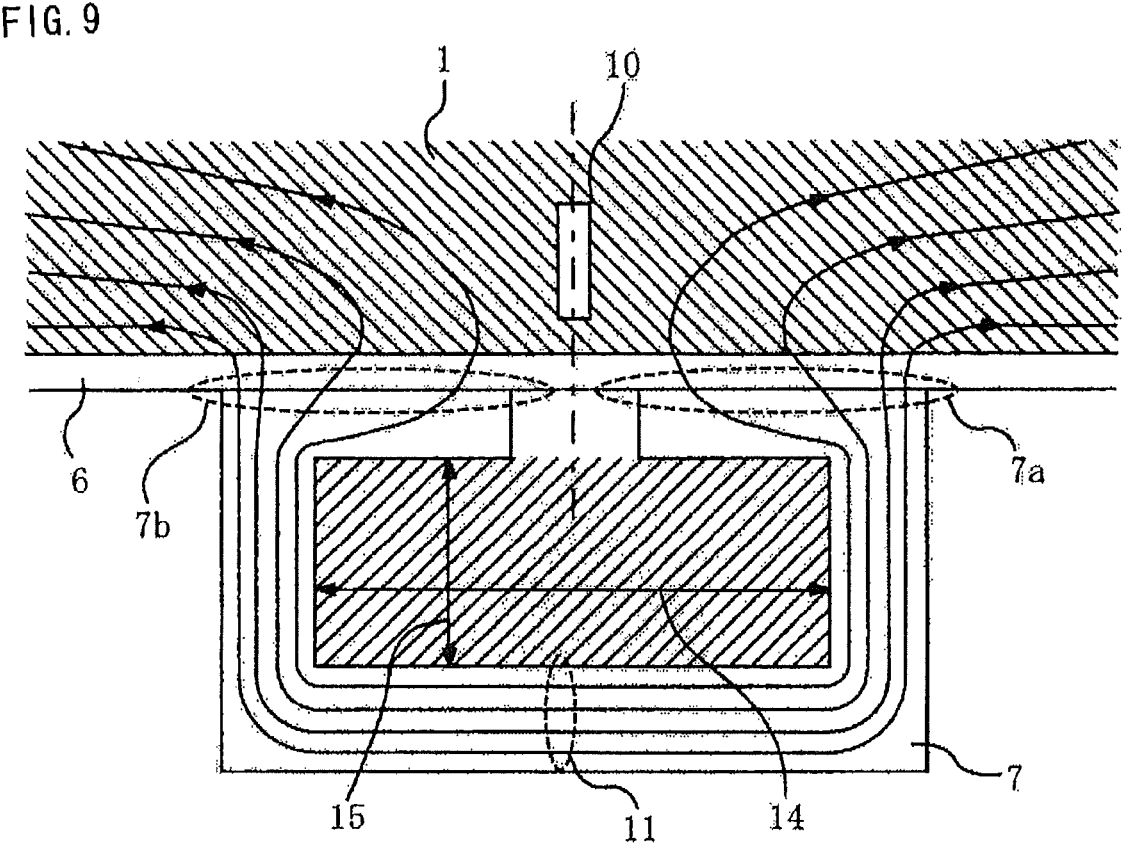
FIG. 9 is an enlarged view showing a flow of local leakage magnetic flux shown in FIG. 8.

FIG. 8 is a cross-sectional schematic view of a wire rope flaw detector with a magnetic path member shown in FIG. 6, and FIG. 9 is an enlarged view showing a flow of the local leakage magnetic flux shown in FIG. 8. As shown in the drawings, the local leakage magnetic flux 11 generated in the vicinity of the damaged portion 10 of the wire rope enters from a magnetic flux entrance/exit surface 7a of the magnetic path member 7, passes through the magnetic path member 7 having the cross-section of the approximate U-shape so as to be linked with the detection coil 8, and returns to the wire rope 1 through a magnetic flux entrance/exit surface 7b. Since the large portion of the leakage magnetic flux 11 passes through the magnetic path member 8 made of the ferromagnetic material, the permeance of the magnetic path of the leakage magnetic flux 11 is high, and accordingly, an amount of the leakage magnetic flux is increased compared to that passing through a magnetic path made of a non-magnetic material. Further, when the magnetic path of the leakage magnetic flux 11 is caused to detour in the axial direction and in the radial direction of the wire rope, a length of the magnetic path of the leakage magnetic flux 11 can be extended. Accordingly, the axial direction length 14, and the radial direction length 15 of the magnetic path member 7, which constitute the disposition area 13 of the detection coil, can be increased, whereby the number of turns of the detection coil 8 can be increased significantly. As a result, when the damaged portion 10 of the wire rope passes near the detection coil 8, a higher induced voltage can be obtained compared to a case without the magnetic path member 7, and thus it is possible to ensure an SN ratio necessary to detect the damaged portion 10 of the wire rope.

Figure 10:
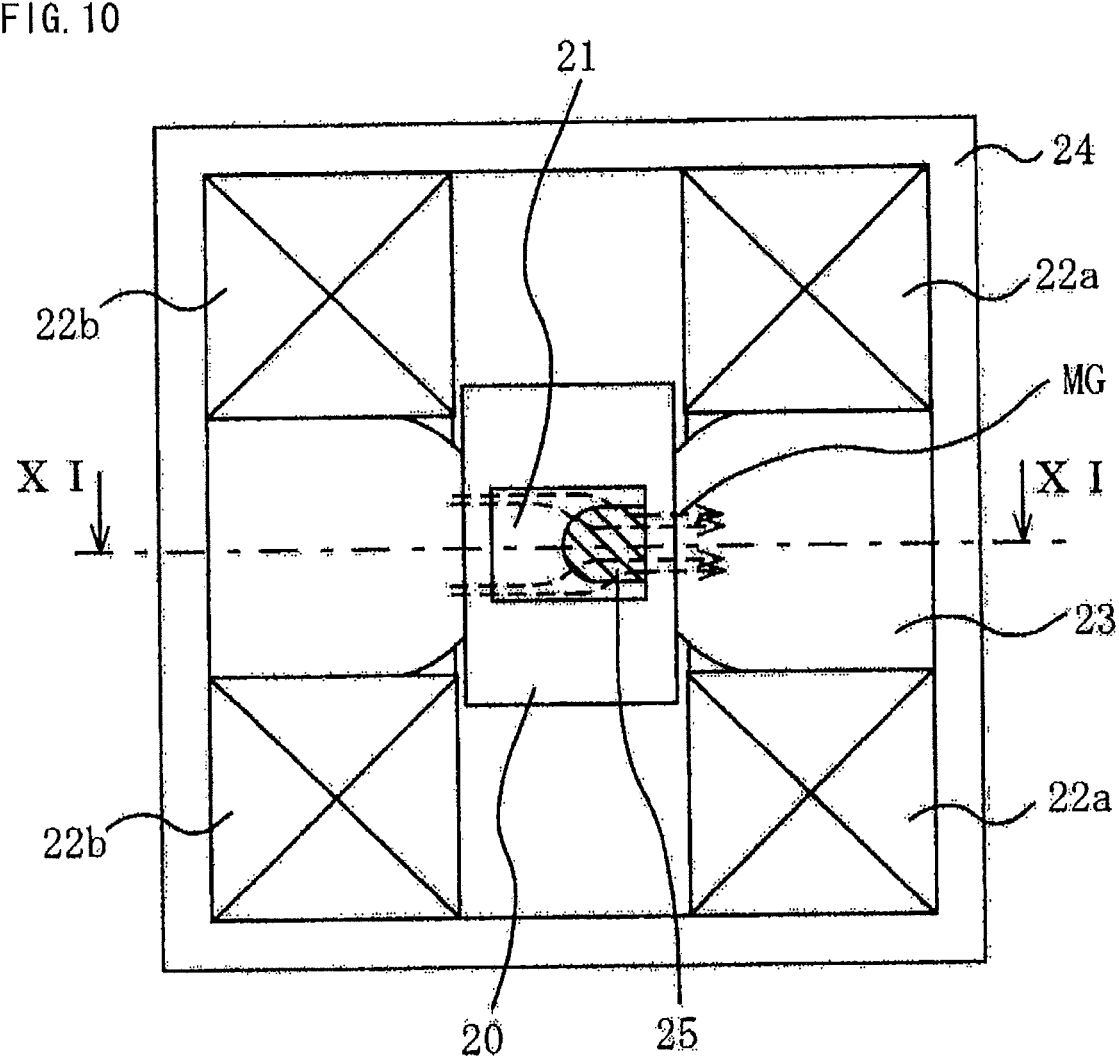
FIG. 10 is a plane cross-sectional view showing an exciting permanent magnet manufacturing apparatus according to embodiment 1 of the present invention.
Figure 11:
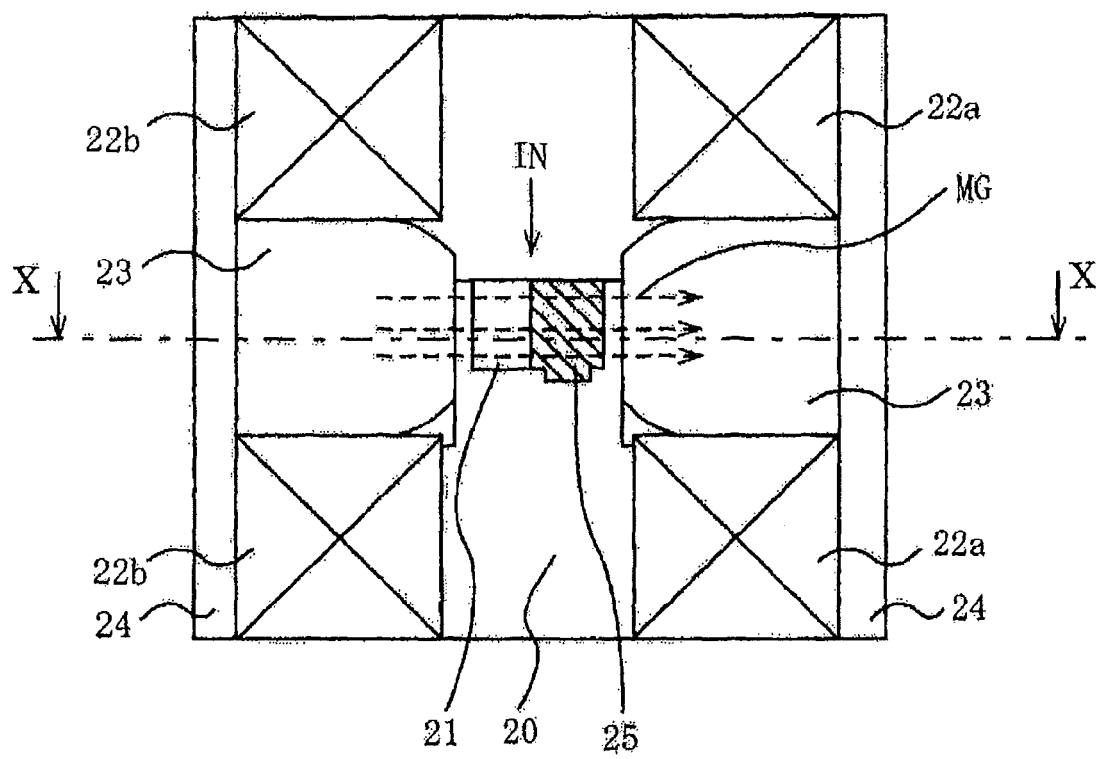
FIG. 11 is a side cross-sectional view showing the exciting permanent magnet manufacturing apparatus according to embodiment 1 of the present invention.

Next, a method for manufacturing the exciting permanent magnet according to embodiment 1 of the present invention will be described. FIG. 10 is a plane cross-sectional view (cross-sectional view cut along a X-X line shown in FIG. 11) showing an exciting permanent magnet manufacturing apparatus according to embodiment 1. FIG. 11 is a side cross-sectional view (a cross-sectional view cut along a XI-XI line shown in FIG. 10) showing the same exciting permanent magnet manufacturing apparatus.

Figure 12:
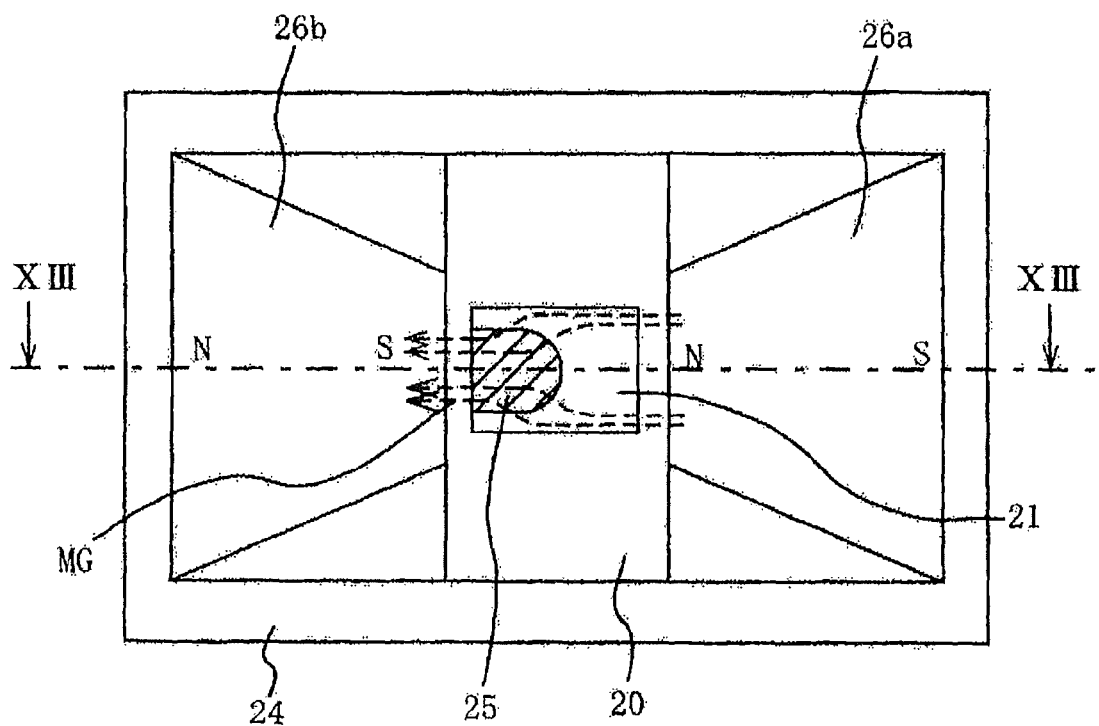
FIG. 12 is a plane cross-sectional view showing the exciting permanent magnet manufacturing apparatus according to embodiment 1 of the present invention.
Figure 13:
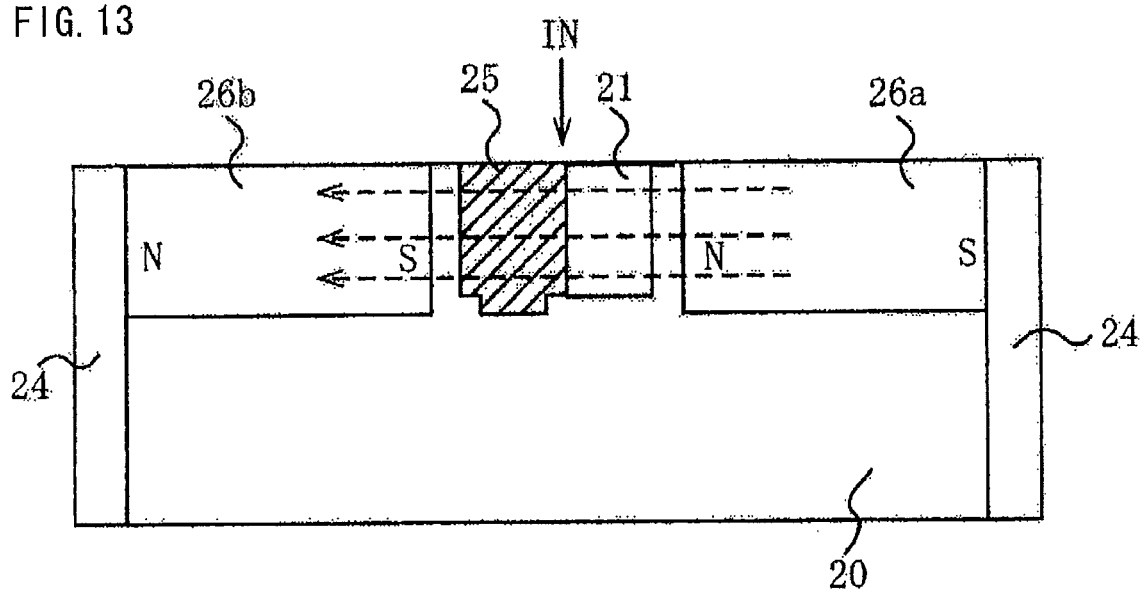
FIG. 13 is a side cross-sectional view showing the exciting permanent magnet manufacturing apparatus according to embodiment 1 of the present invention.

The exciting permanent magnet manufacturing apparatus according to the present embodiment includes a die 20 which is made of a non-magnetic member and forms a cavity 21, a pair of electromagnetic coils 22a and 22b for generating a magnetic field, pole pieces 23 which are made of a ferromagnetic member and cause the magnetic field to converge at the cavity 21, a back yoke 24, and a ferromagnetic member 25 which is made of iron or the like and is disposed within the cavity 21. The exciting permanent magnets 4a and 4b according to the present embodiment are manufactured, with the use of the manufacturing apparatus shown in FIGS. 10 and 11, by bonding Sm—Fe—N magnetic powder with nylon 12 to form a plastic magnet molding material, and by injection-molding the plastic magnet molding material into the die 20. As shown in FIG. 10, the cavity 21, into which the plastic magnet molding material is injected, is surrounded by the ferromagnetic member 25 having a plane cross-section of a U-shape, and the die 20 made of the non-magnetic member. The electromagnetic coils 22a and 22b are magnetic field generation means for aligning a magnetic orientation of the magnet molding material injected into the cavity 21 (for aligning the direction of an axis of easy magnetization). As shown in FIGS. 12 and 13, permanent magnets 26a and 26b for orientation alignment may be disposed as the magnetic field generation means instead of the electromagnetic coils 22a and 22b. FIG. 12 is a schematic view showing a manufacturing apparatus including a permanent magnet as the magnetic field generation means, and FIG. 13 is a cross-sectional view cut along a XIII-XIII line shown in FIG. 12.

In the above exciting permanent magnet manufacturing apparatus (shown in FIGS. 10 to 13), since the ferromagnetic member 25 having the U-shaped plane cross-section is disposed in the cavity 21, magnetic field lines generated from the magnetic field generation means passes through the cavity 21 and converges at the ferromagnetic member 25. That is, the magnetic field generated in the cavity 21 has a distribution indicated by magnetic field lines MG shown in FIG. 10 or 12, and the axis of easy magnetization of the plastic magnet molding material injected into the cavity 21 is aligned with the direction of the magnetic field lines MG. The plastic magnet having such an axis of easy magnetization is magnetized, whereby it is possible to manufacture the exciting permanent magnets 4a and 4b each having a magnetic orientation oriented toward the inside of its U-shape.

Figure 14:
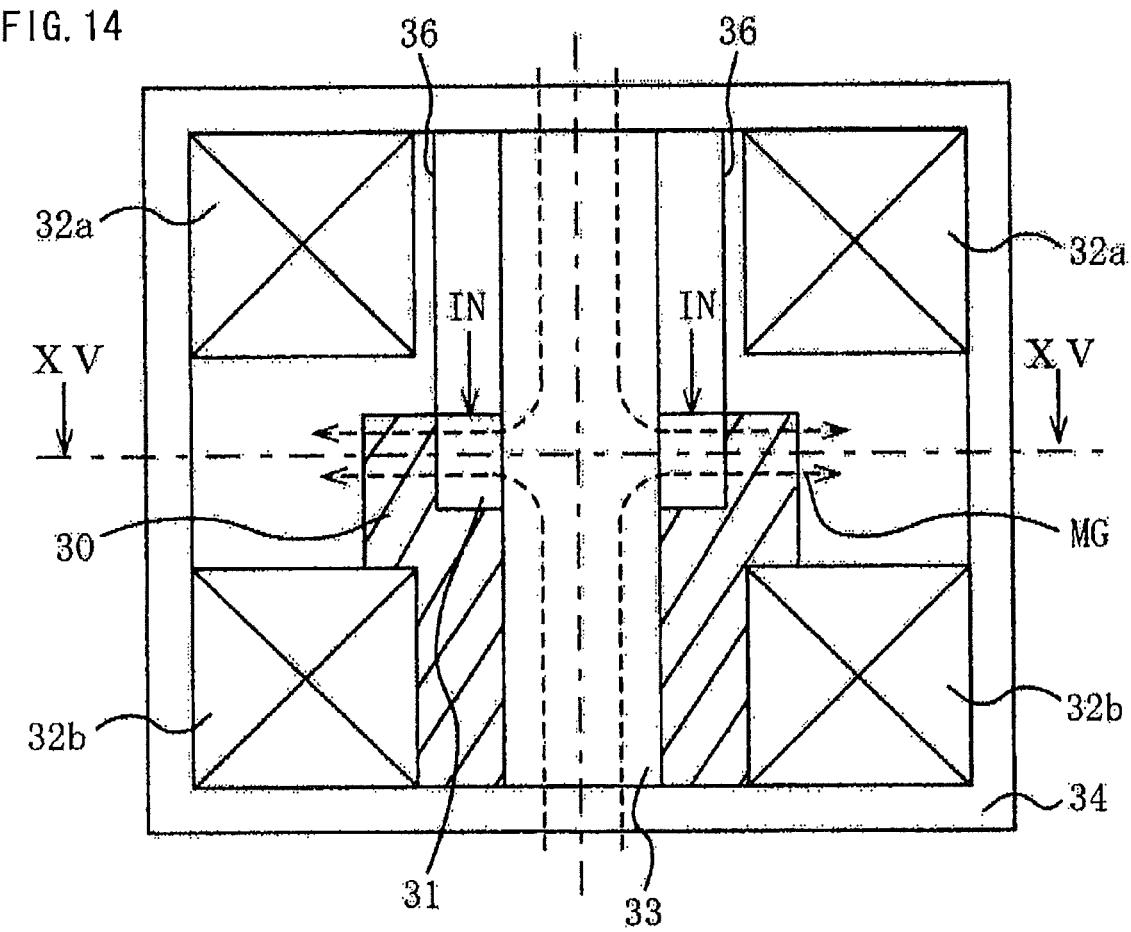
FIG. 14 is a side cross-sectional view showing another exciting permanent magnet manufacturing apparatus according to embodiment 1 of the present invention.

Next, another method for manufacturing the exciting permanent magnet according to embodiment 1 of the present invention will be described. FIG. 14 is a side cross-sectional view showing another exciting permanent magnet manufacturing apparatus according to present embodiment 1, and FIG. 15 is a plane cross-sectional view (cross-sectional view cut along a XV-XV line shown in FIG. 14) of said another exciting permanent magnet manufacturing apparatus.

Figure 15:
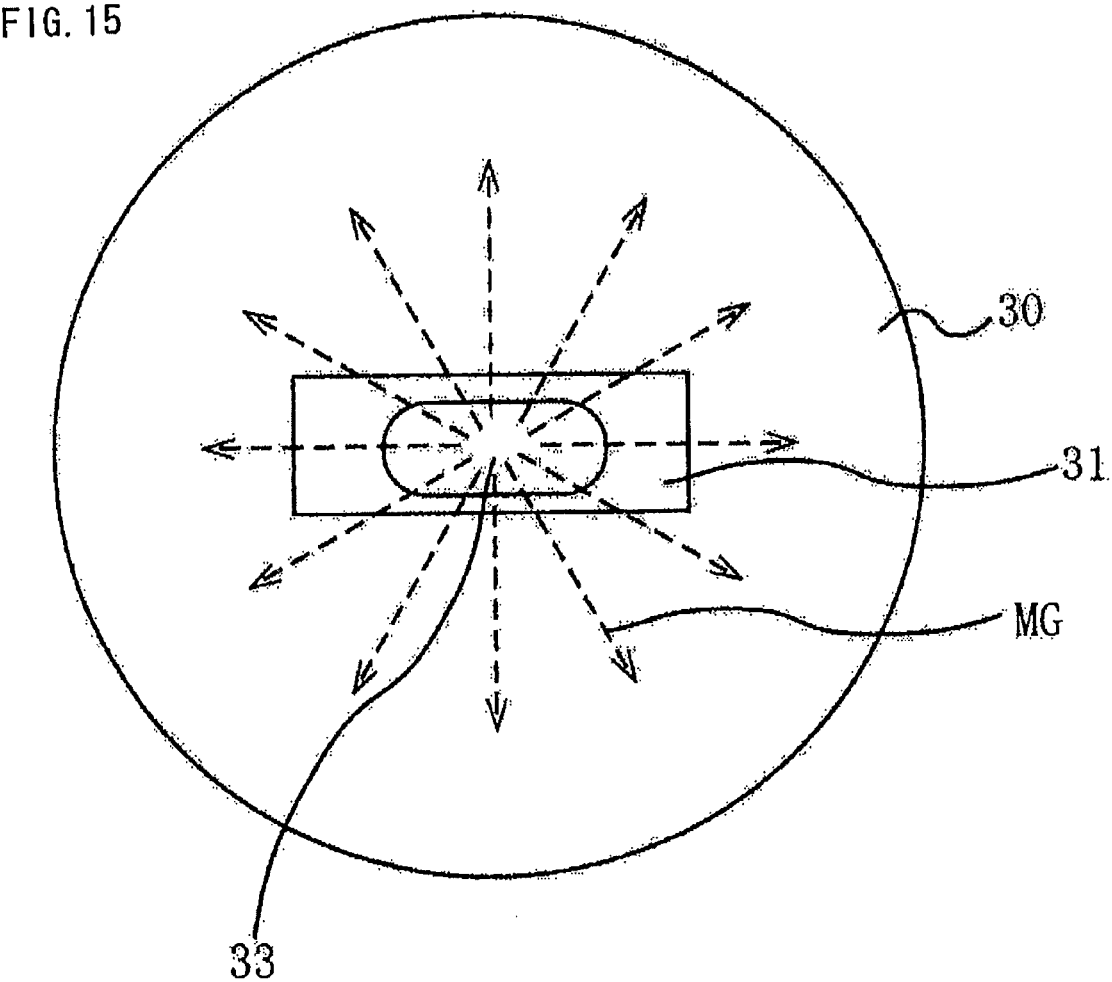
FIG. 15 is a plane cross-sectional view showing another exciting permanent magnet manufacturing apparatus according to embodiment 1 of the present invention.

The exciting permanent magnet manufacturing apparatus shown in each of FIGS. 14 and 15 includes a die 30 forming a cavity 31, a pair of electromagnetic coils 32a and 32b which are arranged one above the other so as to generate a magnetic field, a core 33 made of a ferromagnetic member so as to cause the magnetic field to converge at the cavity 31, and a back yoke 34. As shown in FIG. 15, the core 33 made of the ferromagnetic member has a racetrack shaped cross-section as viewed from a plane surface. In order to manufacture the exciting permanent magnets 4a and 4b, the plastic magnet molding material, which is made by bonding Sm—Fe—N magnetic powder with nylon 12, is injection-molded into the cavity 31 of the die 30. An outer circumference of the cavity 31 into which the plastic magnet molding material is injected is surrounded by a ferromagnetic member having a rectangular cross-section, and an inner circumference thereof is surrounded by a ferromagnetic member having a cross-section of a racetrack shape. Accordingly, a magnetic circuit is formed in which magnetic fields, which are generated by electromagnetic coils 32a and 32b, respectively, and face each other, pass through the core 33, which is the ferromagnetic member having the racetrack shaped plane cross-section, and the cavity 31, and then flow to the outer circumference. Therefore, as indicated by the magnetic field lines MG shown in FIG. 15, a magnetic field is distributed radially (in a radial direction) in the cavity 31 as viewed from the plane surface, and based on the magnetic field, the axis of easy magnetization of the magnet molding material, which is injected into the cavity 31, is aligned in the direction of the above-described magnetic field lines.

Figure 16:
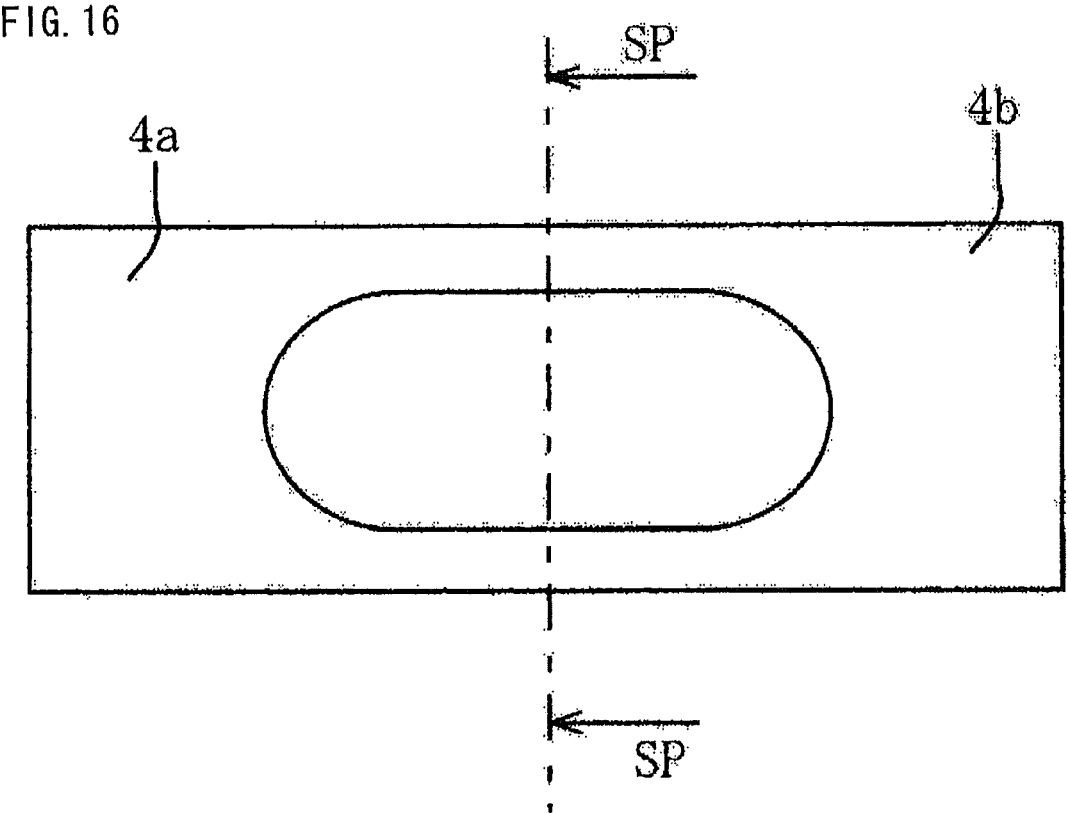
FIG. 16 is a diagram showing a magnet molding molded with the manufacturing apparatus shown in each of FIGS. 14 and 15.

The plastic magnet having such an axis of easy magnetization is magnetized, whereby it is possible to manufacture a plastic magnet molding having a magnetic orientation oriented toward the center of the racetrack shaped cross-section. As shown in FIG. 16, when the above plastic magnet molding is cut along a splitting surface SP through a machining process, it is possible to manufacture a pair of exciting permanent magnets 4a and 4b with one manufacturing process, which enhances productivity.

Further, when a sintered magnet, which has a ferromagnetic property, is used as the exciting permanent magnets 4a and 4b, a larger amount of magnetic flux flows through the wire rope 1 in an effectively improved manner. Here, a method for manufacturing the sintered magnet used as the exciting permanent magnets 4a and 4b will be described. First, a rare earth magnet alloy is manufactured by using a die casting method, a strip casting method, or the like. The alloy undergoes a hydrogen brittleness process, and is then pulverized into a fine powder having an average particle size of 3 to 5 μm by using a jet mill, a ball mill, a Braun mill, or the like. The fine powder undergoes a compacting process by using a die arranged in a magnetic field of 1T or more, to manufacture a preliminary compact. The preliminary compact is introduced into a vacuum heat treat furnace, sintered at about 1100 degrees, and then heat-treated at about 500 degrees. The heat-treated sintered compact is magnetized, whereby the sintered magnet, which corresponds to the exciting permanent magnets 4a and 4b, is manufactured.

Figure 17:
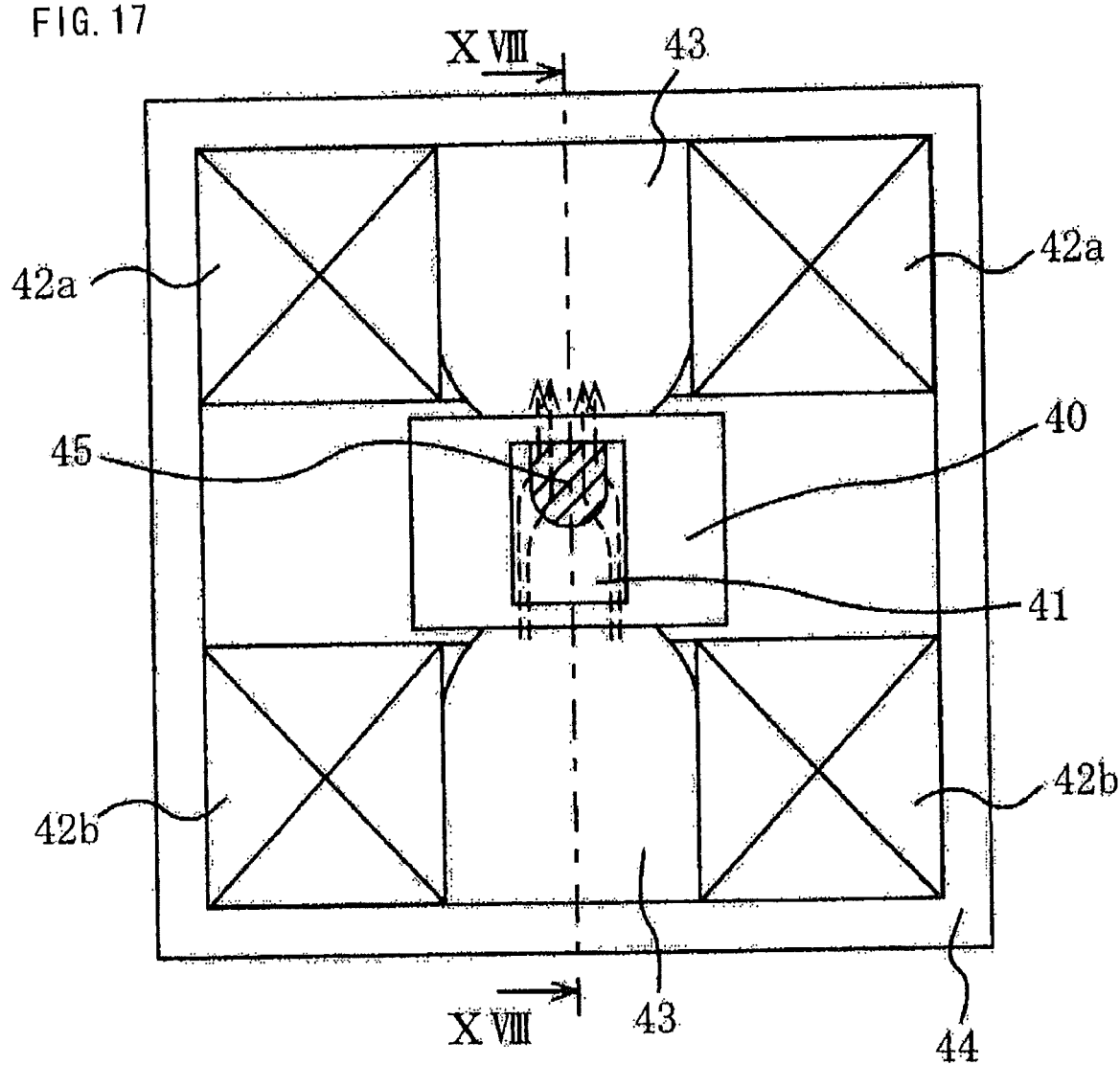
FIG. 17 is a side cross-sectional view showing an exciting permanent magnet manufacturing apparatus for manufacturing a sintered magnet according to embodiment 1 of the present invention.
Figure 18:
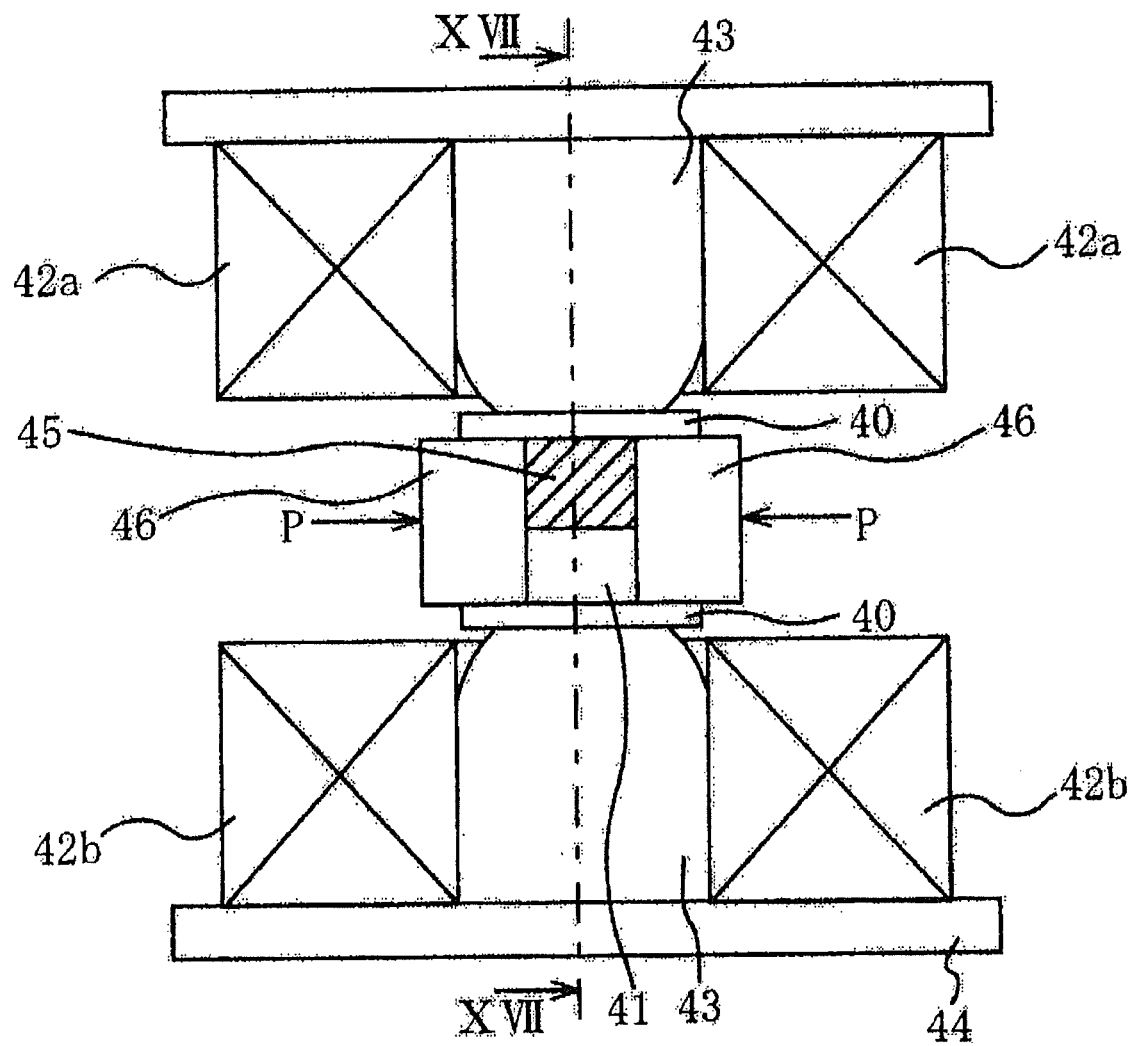
FIG. 18 is a side cross-sectional view showing the exciting permanent magnet manufacturing apparatus for manufacturing the sintered magnet according to embodiment 1 of the present invention.

FIG. 17 is a side cross-sectional view (cross-sectional view cut along a XVII-XVII line shown in FIG. 18) of an exciting permanent magnet manufacturing apparatus for manufacturing the sintered magnet. FIG. 18 is a side cross-sectional view (cross-sectional view cut along a XVIII-XVIII line shown in FIG. 17) of the same exciting permanent magnet manufacturing apparatus for manufacturing the sintered magnet. In each of the FIGS. 17 and 18, a cavity 41 of a die 40 is filled with a fine powdery magnet alloy. A pair of electromagnetic coils 42a and 42b, which are magnetic field generation means disposed one above the other, generates a magnetic field of 1T or more in the cavity 41 so as to align a magnetic orientation of the magnetic powder, and also to manufacture a preliminary compact by compacting the magnetic powder with the use of a punch 46. In this case, a ferromagnetic member 45 having a U-shaped side cross-section is disposed in the cavity 41, and thus the magnetic field lines generated by the magnetic field generation means are aligned as indicated by arrows in FIG. 17, and the axis of easy magnetization of the magnet alloy in the cavity 41 is aligned in the direction of the above-described magnetic filed lines. Thereafter, the preliminary compact undergoes sintering, heat treatment, and magnetization, whereby the exciting sintered magnet having the same magnetic orientation as the above plastic magnet is manufactured.

Figure 19:
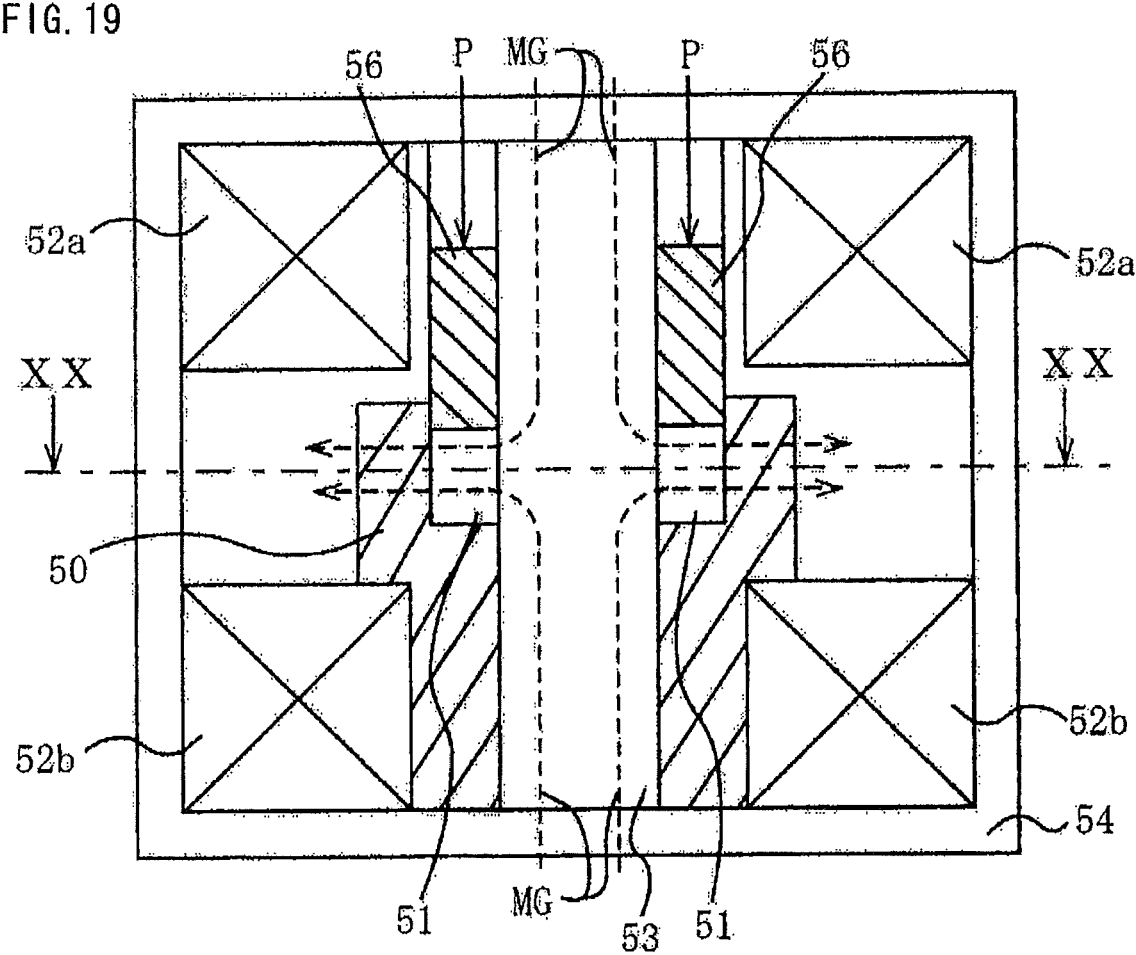
FIG. 19 is a side cross-sectional view showing another exciting permanent magnet manufacturing apparatus for manufacturing the sintered magnet according to embodiment 1 of the present invention.
Figure 20:
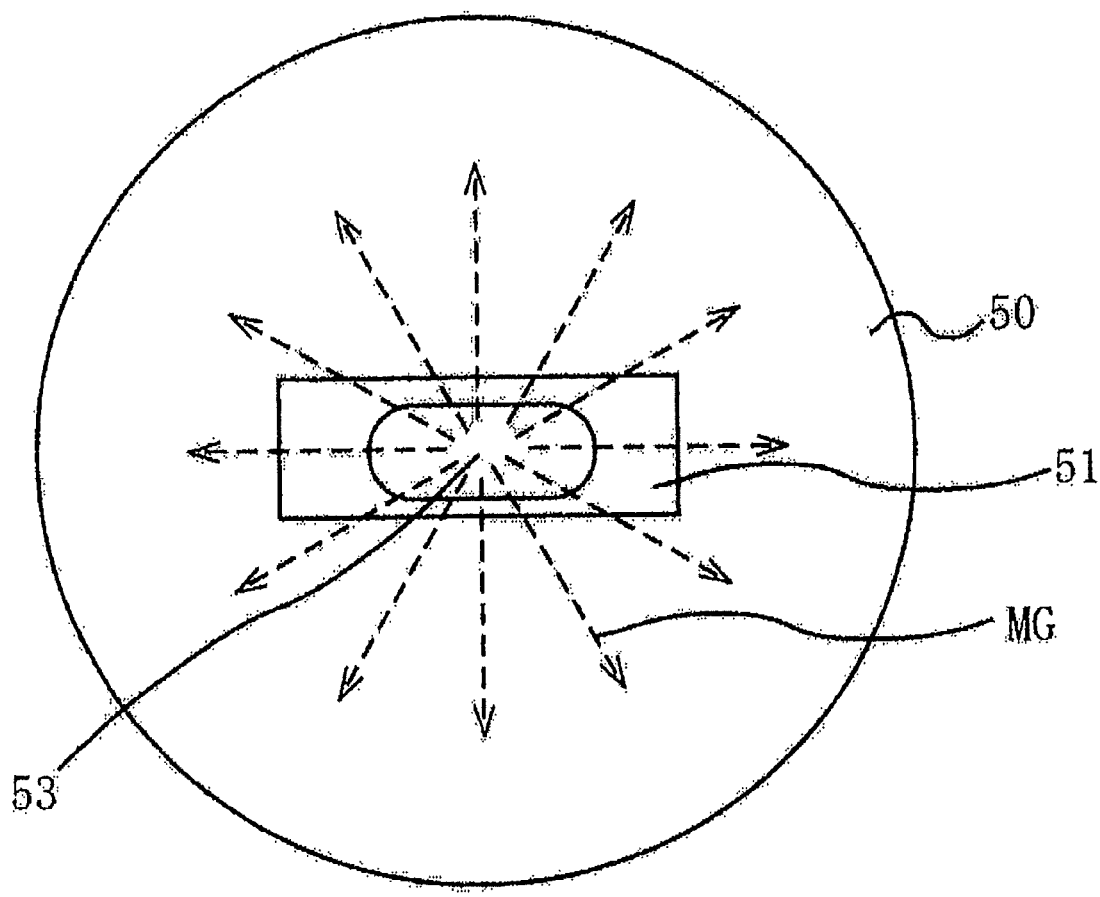
FIG. 20 is a plane cross-sectional view showing another exciting permanent magnet manufacturing apparatus for manufacturing the sintered magnet according to embodiment 1 of the present invention.

FIG. 19 is a side cross-sectional view showing another exciting permanent magnet manufacturing apparatus for manufacturing the sintered magnet, according to present embodiment 1. FIG. 20 is a plane cross-sectional view (cross-sectional view cut along a XX-XX line shown in FIG. 19) showing said another exciting permanent magnet manufacturing apparatus for manufacturing the sintered magnet. In each of FIGS. 19 and 20, a cavity 51 of a die 50 is filled with a fine powdery magnet alloy. A pair of electromagnetic coils 52a and 52b, which are magnetic field generation means disposed one above the other, generate a magnetic field of 1T or more in the cavity 51 so as to align the above magnetic powder, and also to manufacture a preliminary compact by compacting the magnetic powder with the use of a punch 56. In this case, an outer circumference of the cavity 51 is surrounded by a ferromagnetic member (die 50) having a rectangular cross-section, and an inner circumference thereof is surrounded by a ferromagnetic member (core 53) having a racetrack shaped cross-section. Accordingly, a magnetic circuit is formed in which magnetic fields, which are generated by the electromagnetic coils 52*a* and 52*b*, respectively, and face each other, pass through the core 53, which is the ferromagnetic member having the racetrack shaped plane cross-section, and the cavity, and then flow toward the outer circumference. Therefore, as indicated by the magnetic field lines MG shown in FIG. 20, the magnetic field is distributed radially (in the radial direction) in the cavity 51 as viewed from the plane surface, and based on the magnetic field, the axis of easy magnetization of the preliminary compact in the cavity 31 is aligned in the direction of the above-described magnetic field lines. The preliminary compact having the above-described axis of easy magnetization is magnetized, whereby it is possible to manufacture a sintered magnet having a magnetic orientation oriented toward the center of the racetrack shaped cross-section. Further, the sintered magnet is cut through a machining process, whereby a pair of exciting permanent magnets 4*a* and 4*b* are manufactured with only one manufacturing process, which enhances productivity.

In the sintered magnet manufacturing apparatus according to embodiment 1, the magnetic field generated from coils of the magnetic field generation means may be a stationary magnetic field, or a pulse magnetic field. In the case of the pulse magnetic field, in order to reduce loss by eddy-current, it is preferable that a die made of ceramics, rubber, and the like, instead of metal, is used as a die filled with the magnetic powder.

Figure 21:
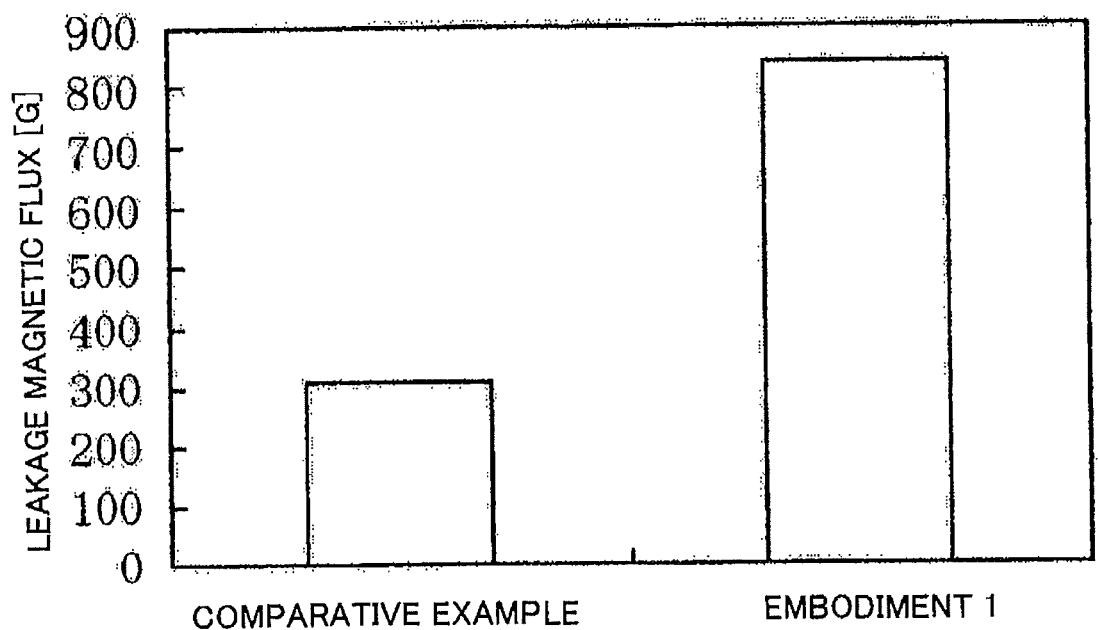
FIG. 21 is a graph showing leakage magnetic flux detected by the wire rope flaw detector according to embodiment 1 of the present invention.
Figure 32:
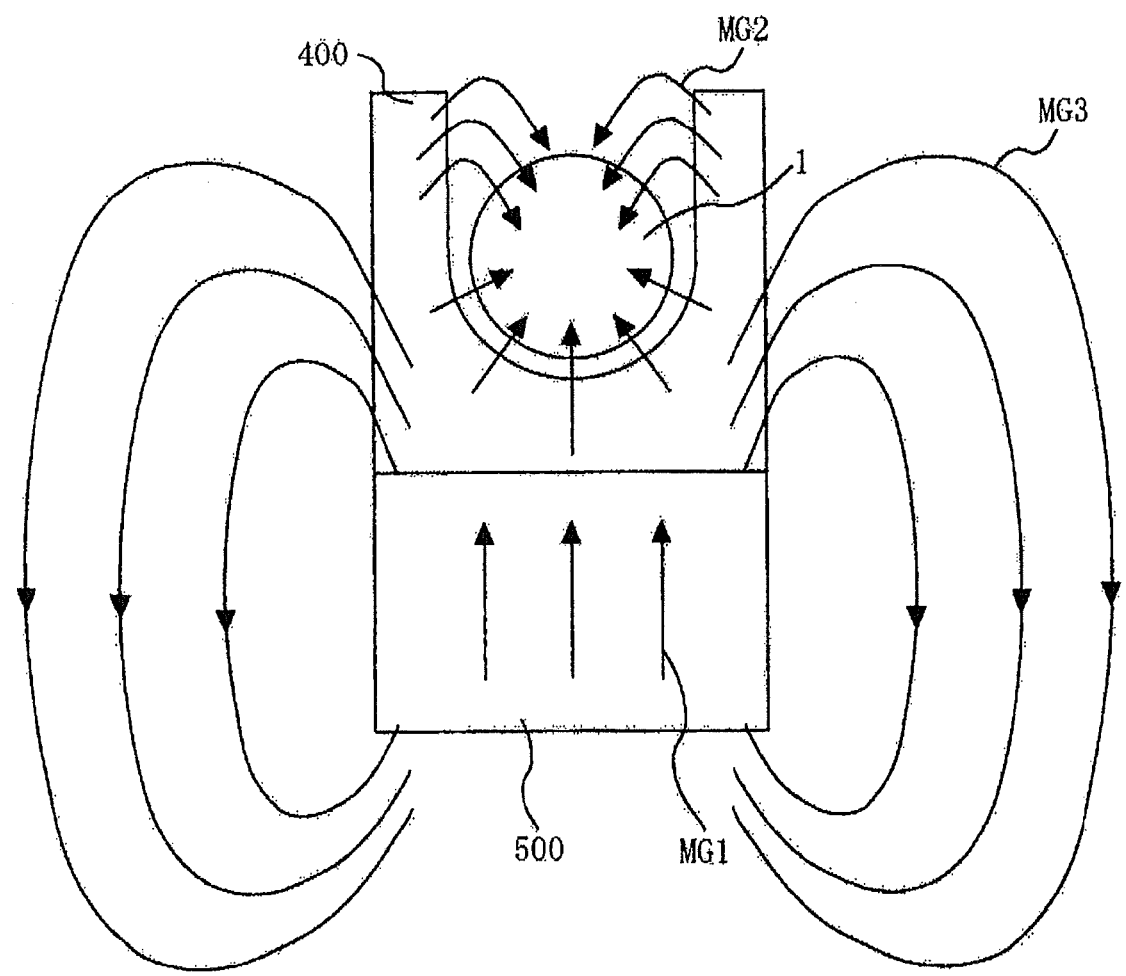
FIG. 32 is a diagram showing a flow of magnetic flux of an exciting permanent magnet of a comparative example.

FIG. 21 is a graph showing leakage magnetic flux detected by the wire rope flaw detector with a permanent magnet according to present embodiment 1. In this case, in order to simulate a damaged portion 10, a pinhole having a diameter of 0.5 mm and a depth of 1 mm is arranged on a side of the wire rope 1 having a diameter of 12 mm. FIG. 21 shows a peak value of the leakage magnetic flux which is linked with the detection coil when the above damaged portion 10 passes directly above the detection coil 8. FIG. 21 also shows, as a comparative example, leakage magnetic flux of a wire rope flaw detector which uses a permanent magnet 500 of a block shape and a magnetic pole piece 400 of an U-shape shown FIG. 32 in a combined manner. Note that a total weight of the permanent magnets used in the present embodiment is the same as that of the permanent magnets used in the comparative example. It is clear from FIG. 21 that the leakage magnetic flux in the case of using the wire rope flaw detector according to the present embodiment is extremely larger than that of the wire rope flaw detector of the comparative example. This is because a larger amount of magnetic flux flows inside the wire rope 1.

Figure 22:
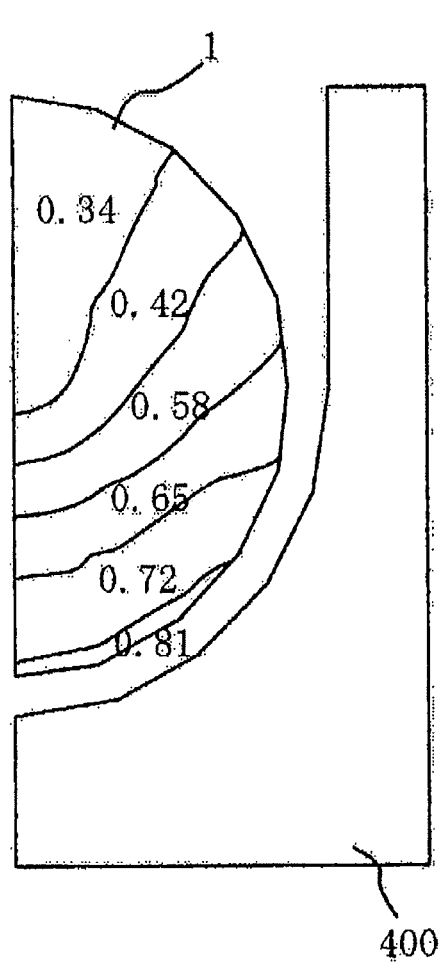
FIG. 22 is a diagram showing analysis results of magnetic flux on a cross-section of the wire rope detected by the wire rope flaw detector according to the present embodiment and its comparative example, the analysis being performed based on a finite element method.
Figure 22:
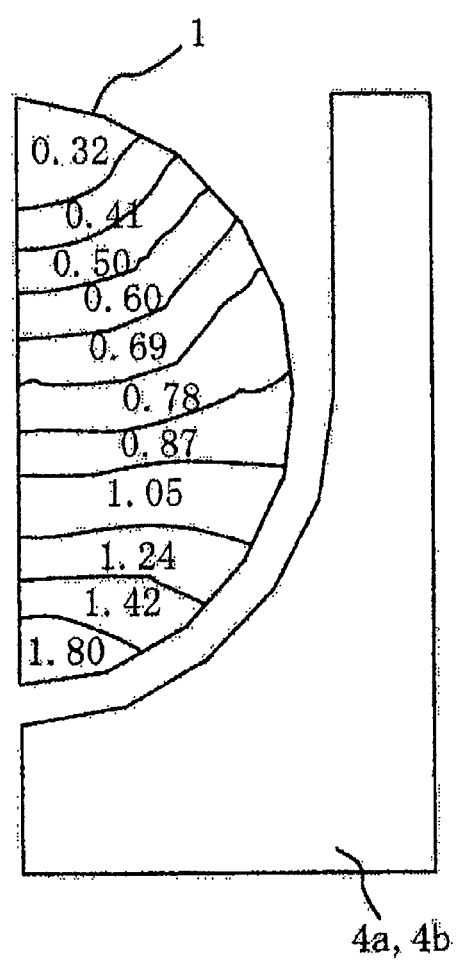

Since the distribution of the magnetic flux inside the wire rope 1 cannot be observed directly, analysis of the distribution of the magnetic flux on the cross-section of the wire rope is performed based on a finite element method with respect to the wire rope flaw detector of the comparative example and the wire rope flaw detector according to the present embodiment, and results of the analysis is shown in FIG. 22. It is clear that the distribution of the magnetic flux density on the cross-section of the wire rope according to the present embodiment is relatively larger than the distribution of the magnetic flux density on the cross-section of the wire rope of the comparative example, and thus the effect of the present embodiment is expressly presented.

Figure 23:
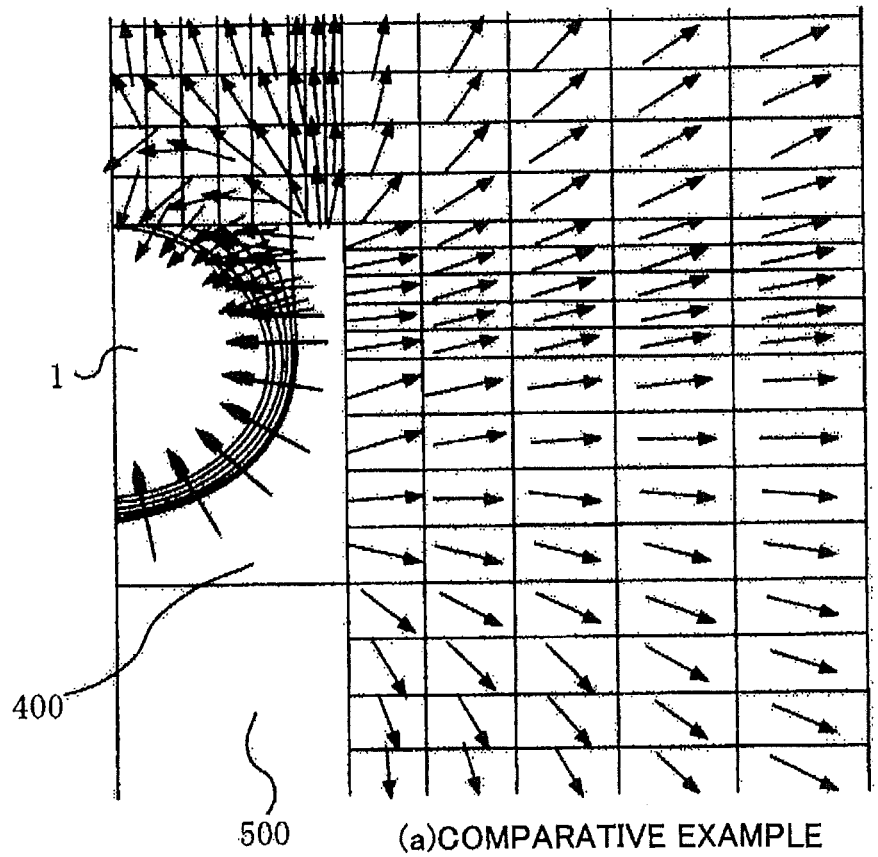
FIG. 23 is a diagram showing analysis results, based on the finite element method, of flow of the magnetic flux leaking in a space other than the back yoke, the exciting permanent magnet, and the wire rope, when the wire rope is excited by the exciting permanent magnets in the wire rope flaw detector according to the present embodiment and its comparative example, the flows being represented by vectors.
Figure 23:
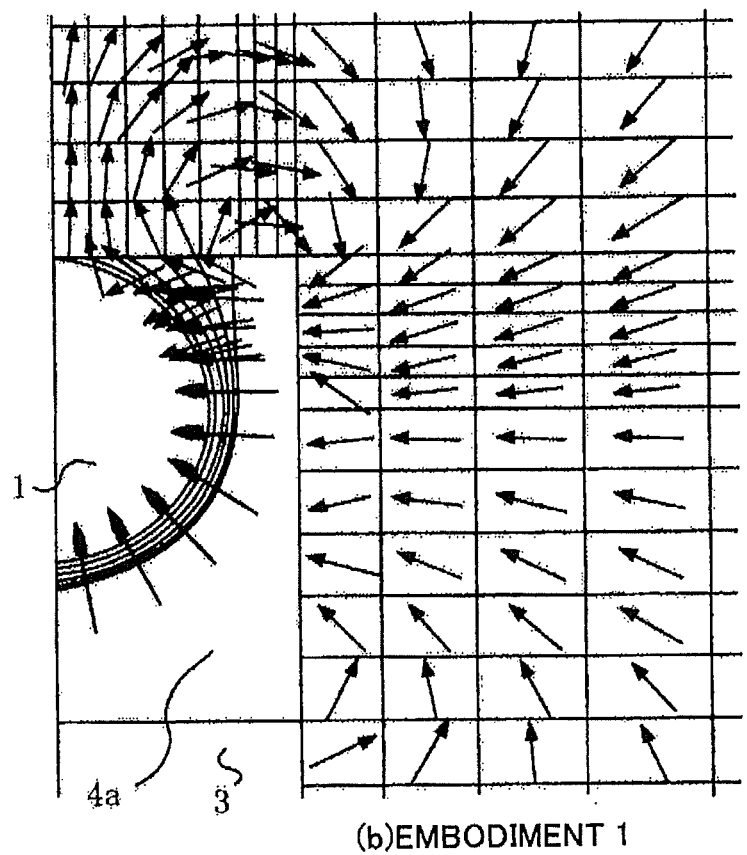

FIG. 23 is a diagram showing analysis results, based on the finite element method, of flows of the magnetic flux leaking in a space other than the back yoke, the exciting permanent magnet, and the wire rope, when the wire rope is excited by the exciting permanent magnets in the wire rope flaw detector according to the present embodiment and its comparative example, the flows being represented by vectors. In the drawing, for the sake of easy viewing, a length of the vectors is fixed regardless of the magnitude of the magnetic flux. In the case of the comparative example, many flows of the magnetic flux generated from the magnets are not directed toward the wire rope, but leaks into a space. On the other hand, in the case of the present embodiment, the direction of the vectors is opposite to that of the comparative example, and a larger amount of magnetic flux generated from the magnets flows into the wire rope.

As above described, the exciting magnets 4*a* and 4*b* used in the present embodiment each has a cross-section of a shape surrounding the wire rope 1 when cut along a plane perpendicular to the axial direction of the wire rope 1, and have magnetic orientation, on the cross-section, oriented from at least two directions to the wire rope. Accordingly, it is possible to reduce the magnetic flux leaking outside the wire rope 1 without flowing thereinto, thereby allowing a larger amount of magnetic flux to flow into the wire rope. Therefore, regardless of the position of the damaged portion of the wire rope, a sufficiently large amount of leakage magnetic flux can be obtained, and accordingly, it is possible to obtain a signal having an SN ratio sufficient to be detected by the leakage magnetic flux detection section.

Embodiment 2

Figure 24:
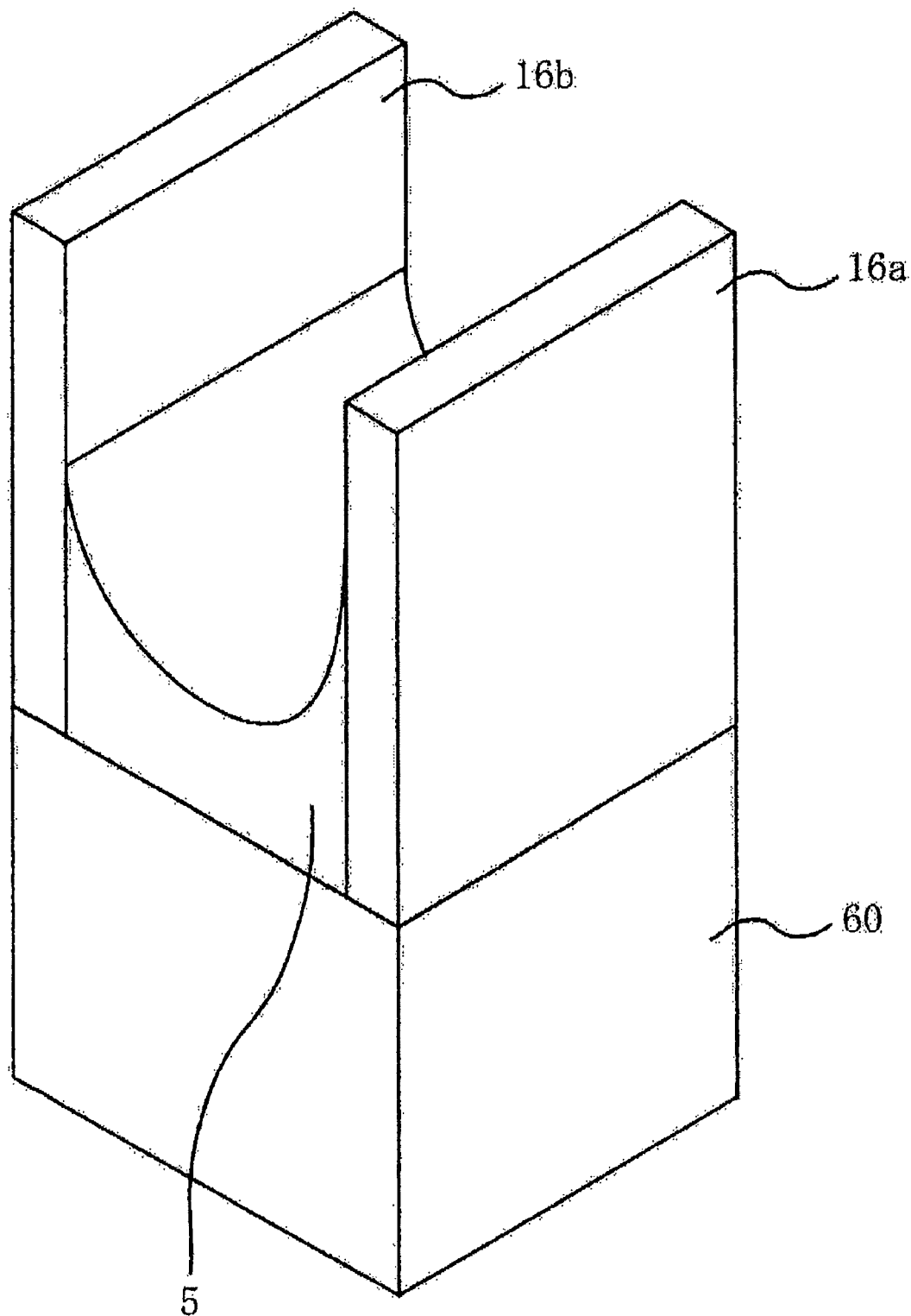
FIG. 24 is a perspective view showing an exciting permanent magnet according to embodiment 2 of the present invention.
Figure 25:
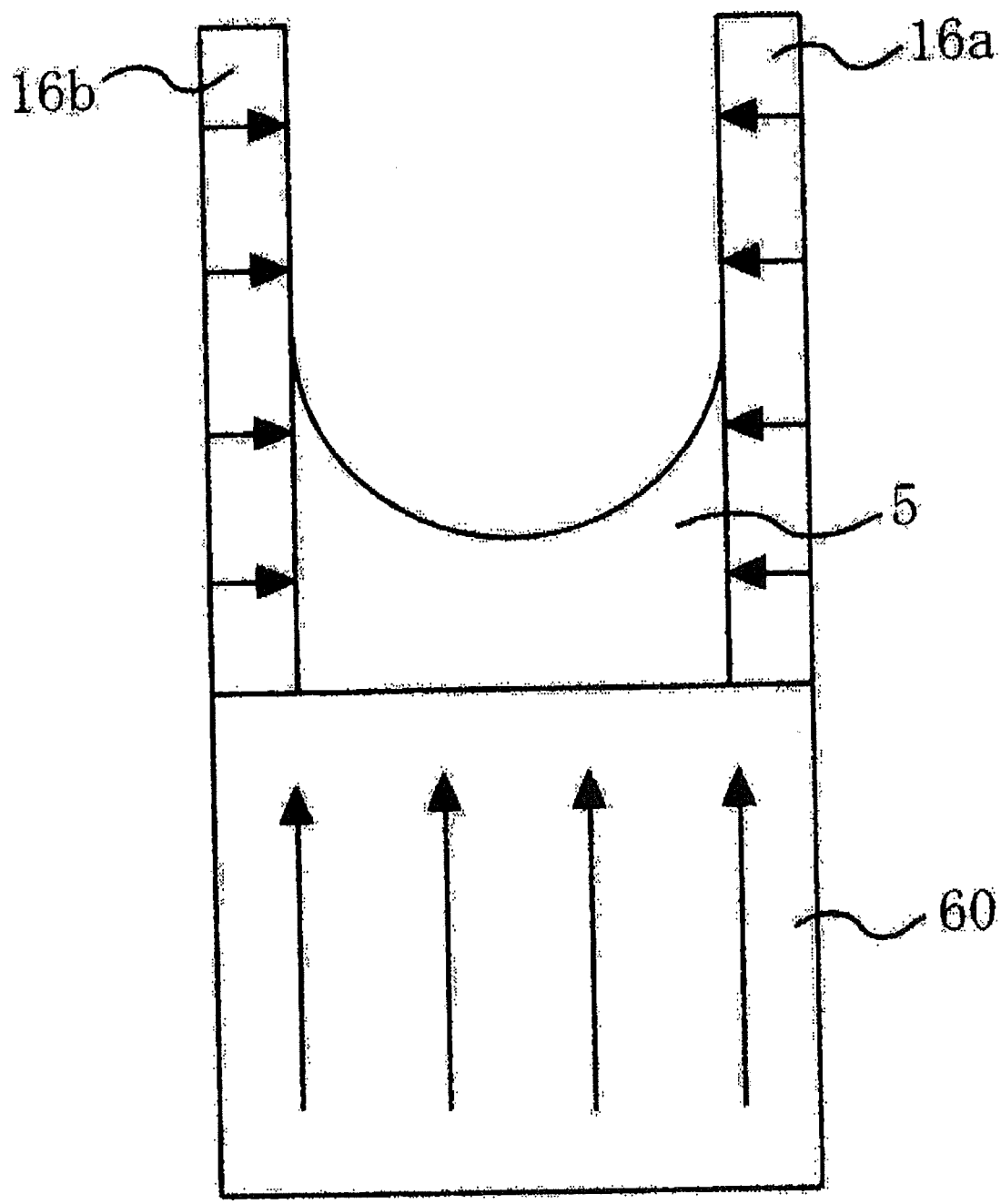

FIG. 24 is a perspective view showing an exciting permanent magnet according to embodiment 2 of the present invention, and FIG. 25 is a cross-sectional view of the exciting permanent magnet shown in FIG. 24 as cut along a plane perpendicular to an axial direction of the wire rope. The exciting permanent magnet according to present embodiment 2 has a configuration in which a magnetic pole piece 5, which has a cross-section of an approximate U-shape when cut along a plane perpendicular to the axial direction of the wire rope, is bonded onto a permanent magnet 60 of a block shape having a length of 15 mm, a width of 15 mm, and a height of 15 mm, with the use of acrylic or epoxide-based adhesive or the like. Auxiliary permanent magnets 16*a* and 16*b*, each of a plate shape having a length of 15 mm, a width of 2.5 mm, and a height of 10 mm, are disposed on the block-shaped permanent magnet 60 and are attached to side surfaces of the magnetic pole piece 5 having the U-shaped cross-section such that polarities of the permanent magnets 16*a* and 16*b* are opposite to each other. As shown in FIG. 25, a magnetic orientation of each of the block-shaped magnet 60 and the plate-shaped magnets 16*a* and 16*b* is aligned in one direction and oriented toward the wire rope 1.

As above described, according to the present embodiment, a plurality of magnets each having a magnetic orientation oriented in one direction are combined, and arranged such that each magnetic orientation on its cross-section cut along a plane perpendicular to the axial direction of the wire rope is oriented toward the wire rope. Accordingly, it is possible to reduce the magnetic flux which is generated from the respective magnets and leaks without flowing into the wire rope, and to increase the amount of the local leakage magnetic flux generated in the vicinity of the damaged portion of the wire rope, which improves an SN ratio of the flaw detection signal.

Figure 26:
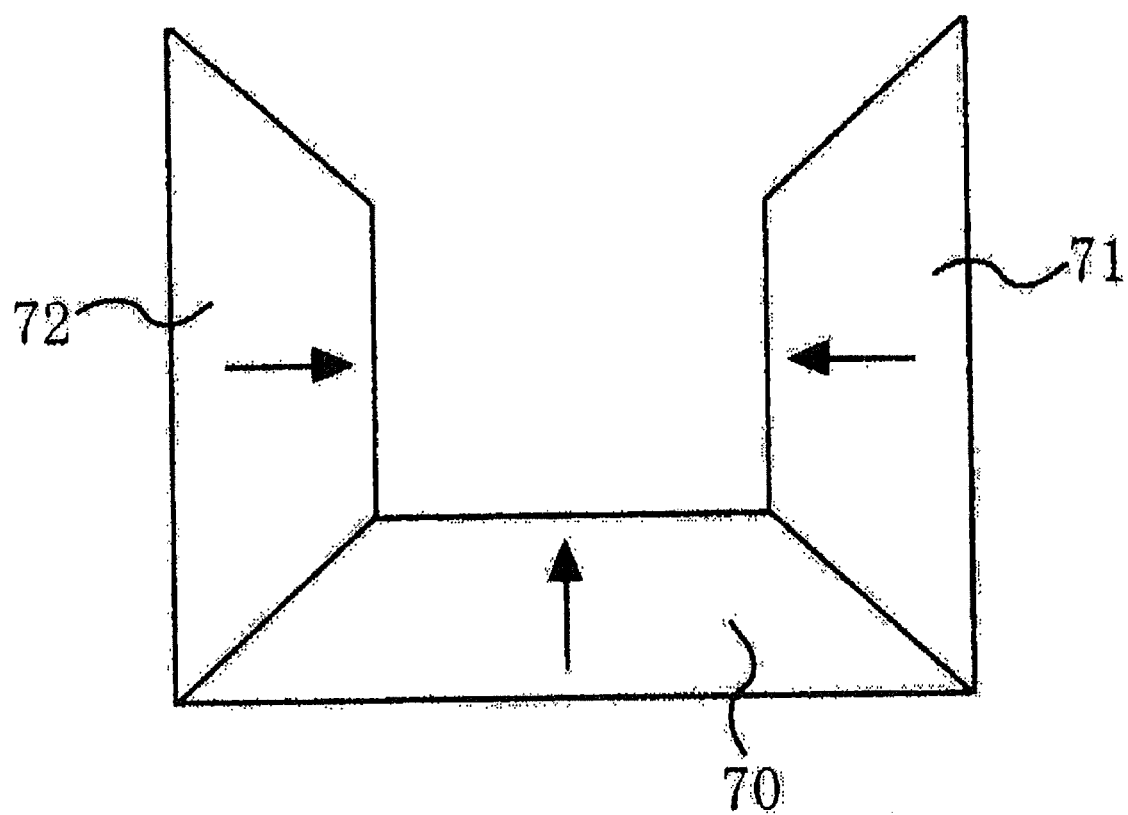

Particularly, the magnet of the block shape and the auxiliary magnets of the plate shape, which are processed easily, are combined together, whereby exciting magnets having a magnetic orientation oriented toward the wire rope 1 can be manufactured inexpensively. As shown in FIG. 26, a similar effect can be obtained when a plurality of permanent magnets 70 to 72 each having a cross-section of a trapezoidal shape are used in a combined manner.

Figure 27:
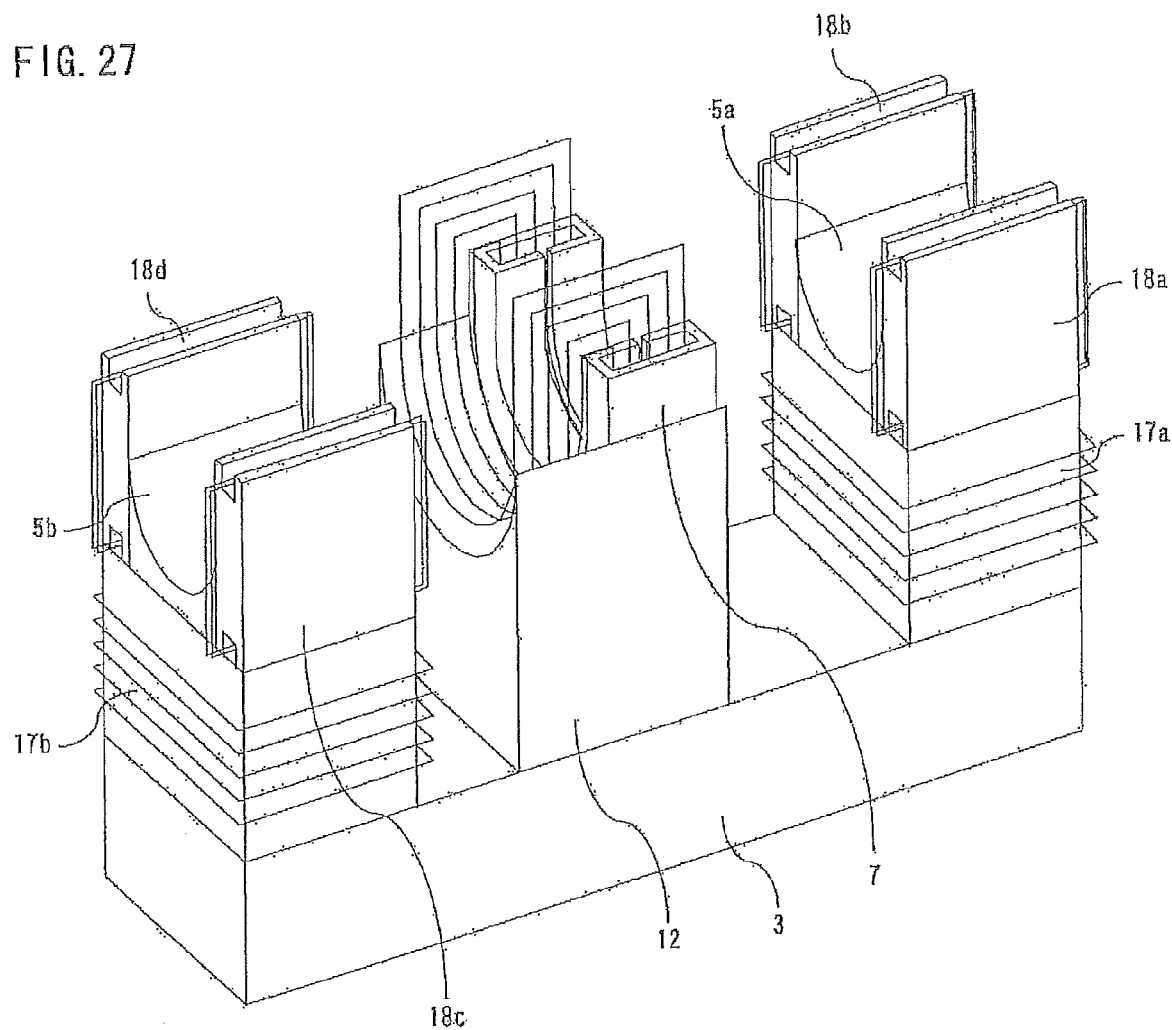
FIG. 27 is a perspective view showing an appearance of another exemplary wire rope flaw detector according to embodiment 2 of the present invention, in a state where a guide plate is removed.

FIG. 27 is a perspective view showing an appearance of another exemplary wire rope flaw detector according to embodiment 2 of the present invention, in a state where a guide plate thereof is removed. In above-described embodiment 1, the block shaped permanent magnet 60 and the plate shaped auxiliary magnets 16a and 16b are used in a combined manner as the exciting magnets. In the wire rope flaw detector shown in FIG. 27, a pair of exciting electromagnets 17a and 17b are disposed on both ends of the back yoke 3, and are excited such that polarities thereof are opposite to each other. Auxiliary electromagnets 18a and 18b each of a plate shape are disposed on the electromagnet 17a, and auxiliary electromagnets 18c and 18d each of a plate shape are disposed on the electromagnet 17b. Magnetic orientations of the auxiliary electromagnet 18a and 18b, and 18c and 18d are set such that polarities of the respective pairs facing the center of the wire rope 1 are the same as those of the electromagnets 17a and 17b.

In this manner, even when the permanent magnet is replaced with the electromagnet, the same effect as above described can be obtained. In this case, when a current to the electromagnet is turned OFF, attractive force is not generated, and thus the work efficiency of an inspection worker is improved when the worker attaches/detaches the wire rope flaw detector to/from the wire rope.

Embodiment 3

Figure 28:
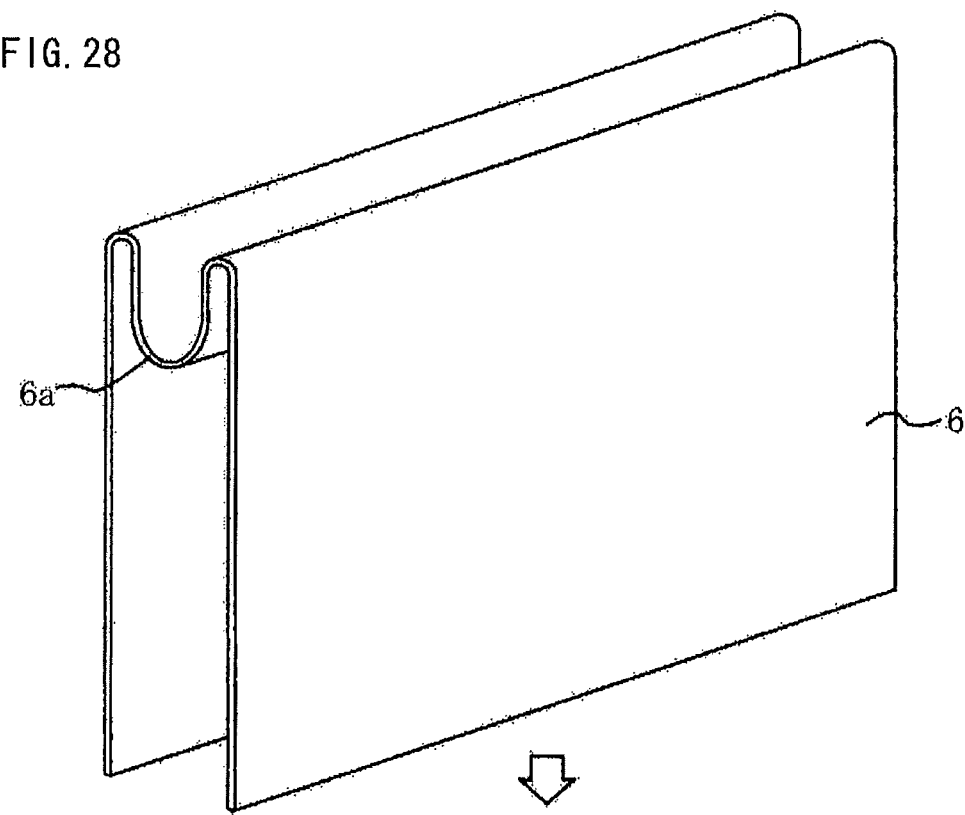
FIG. 28 is a perspective view showing an appearance of a wire rope flaw detector according to embodiment 3 of the present invention, in a state where a guide plate is removed.
Figure 28:
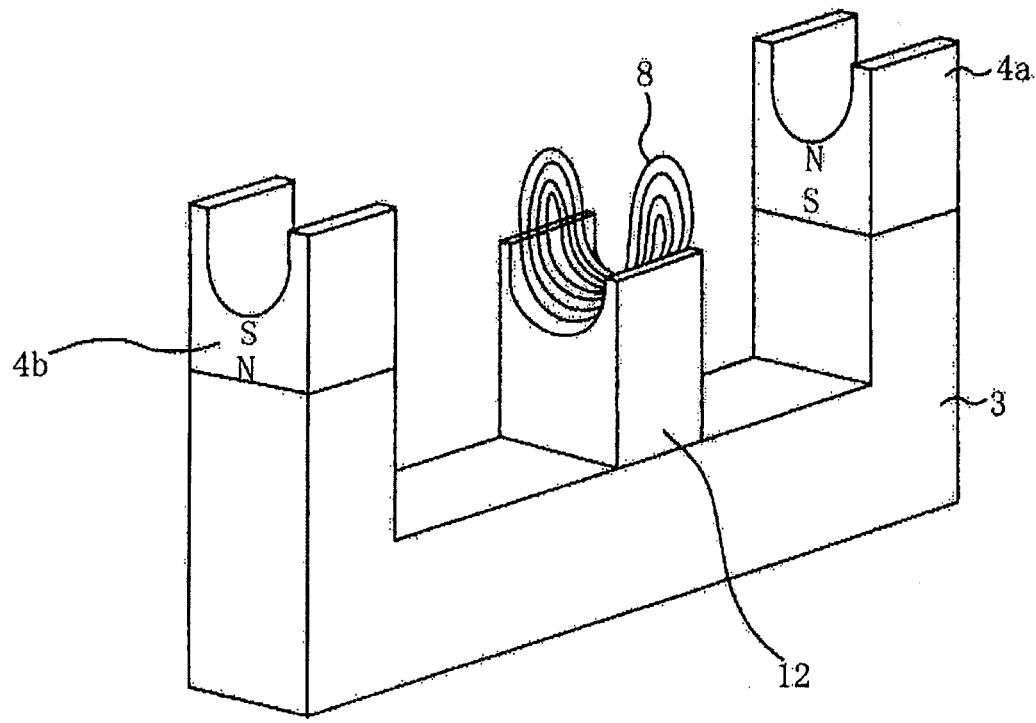
Figure 29:
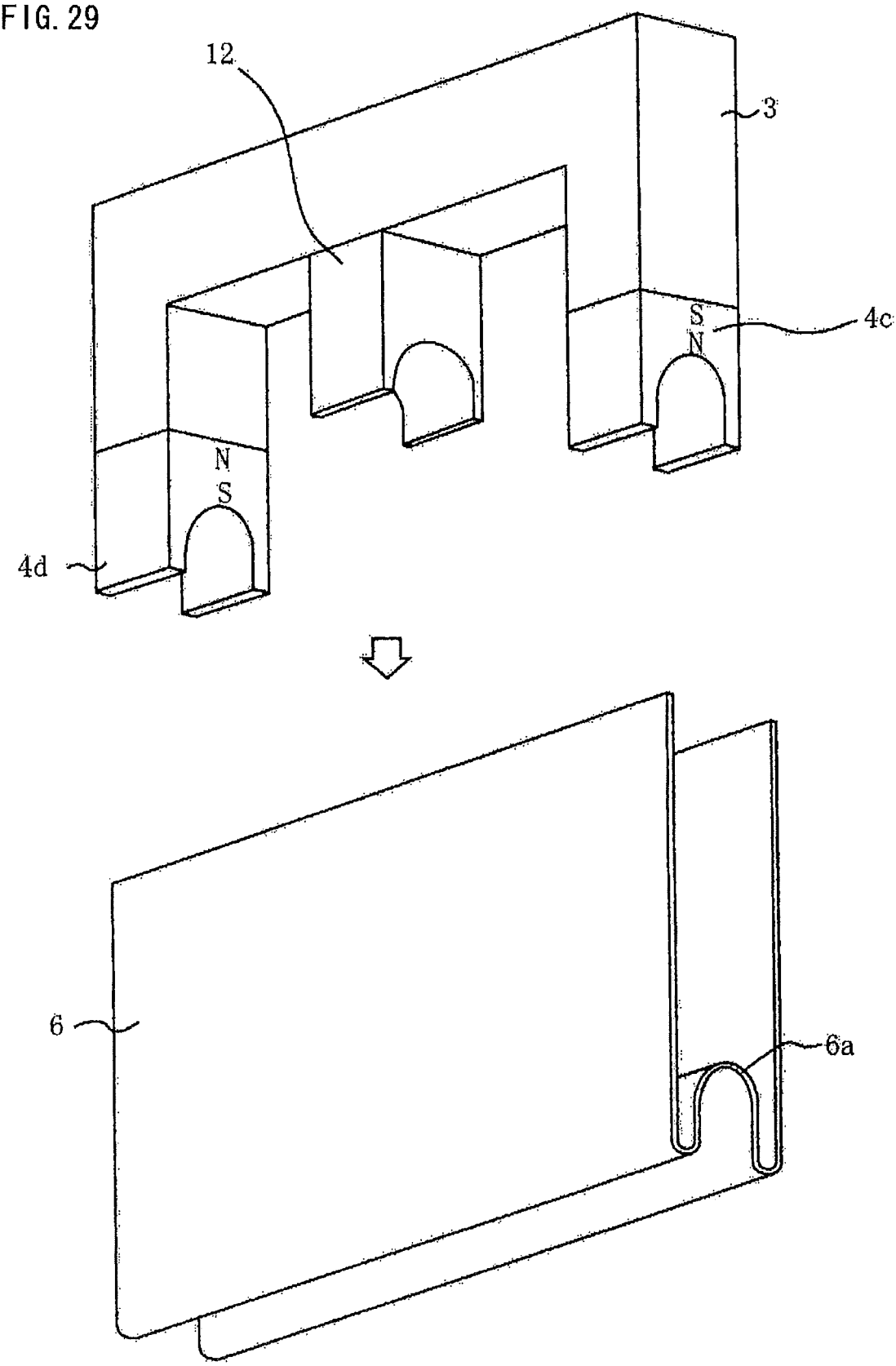
FIG. 29 is a perspective view showing an appearance of a wire rope flaw detector according to embodiment 3 of the present invention, in a state where the guide plate is removed.
Figure 30:
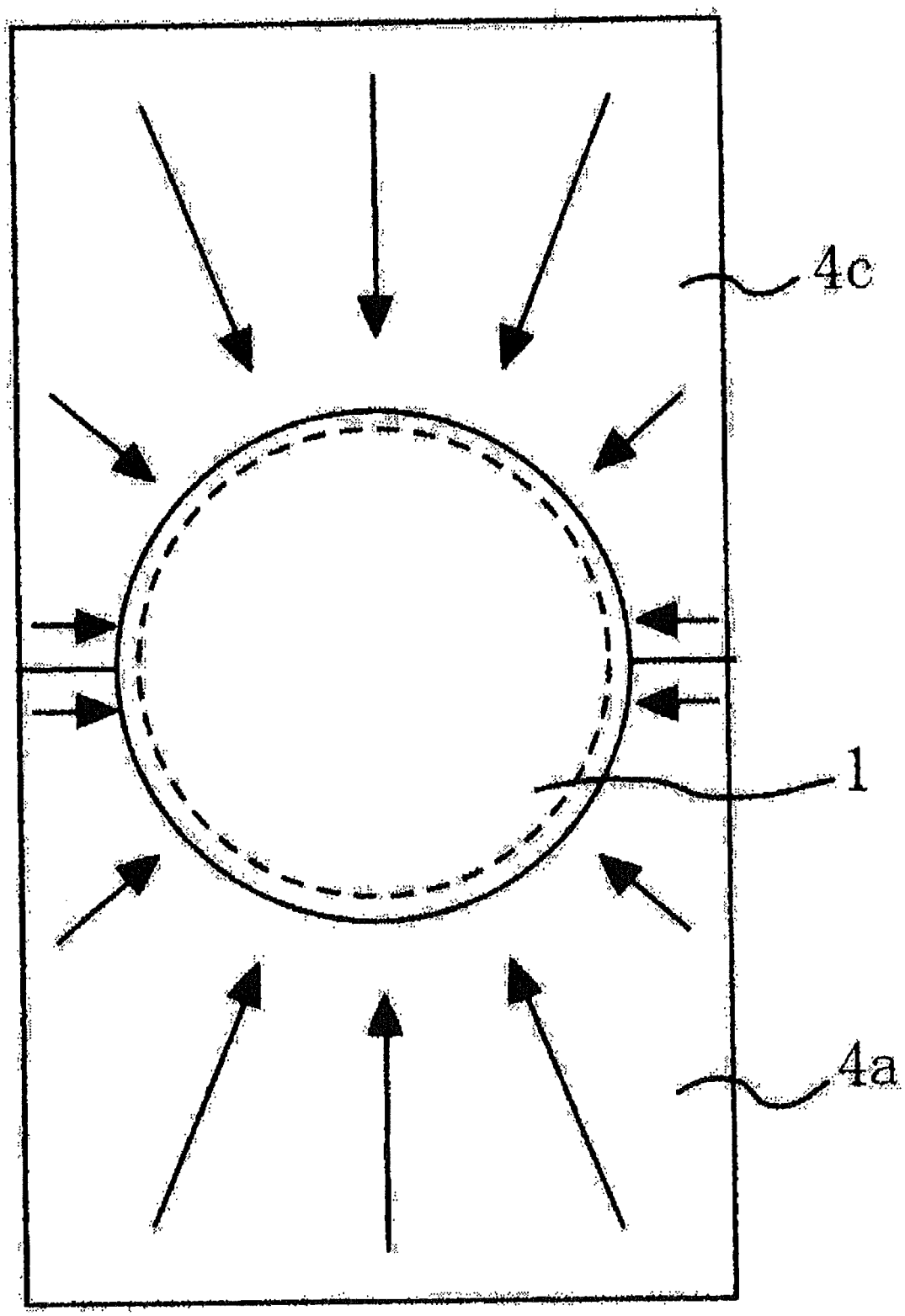
FIG. 30 is a cross-sectional view of an exciting permanent magnet in the wire rope flaw detector according to embodiment 3 of the present invention.

FIGS. 28 and 29 are perspective views each showing an appearance of a wire rope flaw detector according to embodiment 3 of the present invention in a state where a guide plate thereof is removed. FIG. 30 is a cross-sectional view of an exciting permanent magnet in the wire rope flaw detector according to embodiment 3 of the present invention.

The wire rope flaw detector according to embodiment 3 is constituted of a first apparatus, shown in FIG. 28, including a back yoke 3, first exciting permanent magnets 4a and 4b each having a cross-section of an arc shape when cut long a plane perpendicular to an axial direction of a wire rope, a detection coil 8 disposed on a supporting base 12, and a guide plate 6a, and a second apparatus, shown in FIG. 28, including a back yoke 3, second exciting permanent magnets 4c and 4d each having a cross-section of an arc shape when cut along the plane perpendicular to the axial direction of the wire rope, and a guide plate 6. The guide plate 6 included in the first apparatus and that included in the second apparatus are fixed together with a hinge or the like so as to be openable and closable in the wire rope axial direction. Further, the guide plate 6 having the first permanent magnets 4a and 4b bonded thereto and the guide plate 6 having the second permanent magnets 4c and 4d bonded thereto may be fixed with screws so as to be detachable from each other.

As shown in FIG. 30, the first permanent magnets 4a and 4b, and the second permanent magnet 4c and 4d are disposed so as to embrace an outer circumference of the wire rope 1, and to allow magnetic orientations thereof, on a cross-section cut along a plane perpendicular to the axial direction of the wire rope, to be oriented toward the center of the wire rope 1. In this manner, the first and the second permanent magnets have the magnetic orientations oriented toward the center of the wire rope 1, that is, toward the radial direction, and thus a larger amount of magnetic flux is caused to flow into the wire rope 1. Further, the first and the second exciting permanent magnets are disposed so as to embrace the outer circumference of the wire rope 1, whereby a larger amount of magnetic flux is caused to flow into the wire rope, and it is possible to increase local leakage magnetic flux.

Figure 31:
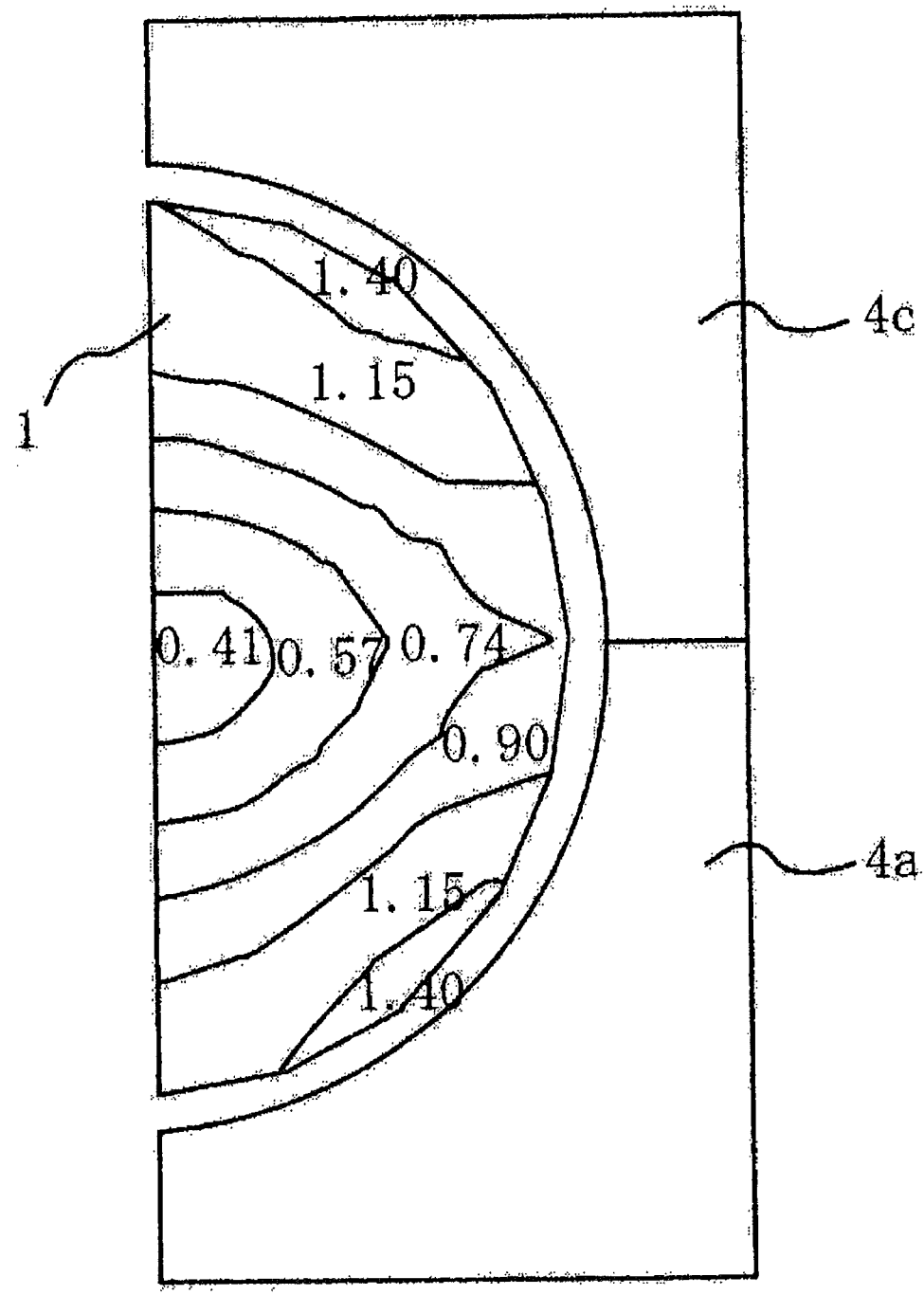
FIG. 31 is a diagram showing an analysis result, based on the finite element method, of magnetic flux distribution on a cross-section of the wire rope in the case where the wire rope flaw detector according to embodiment 3 of the present invention is used.

FIG. 31 shows an analysis result, based on the finite element method, of magnetic flux distribution on a cross-section of the wire rope in the case where the wire rope flaw detector with the exciting permanent magnet according to embodiment 3 is used. Compared to the distribution of the magnetic flux density on the cross-section of the wire rope shown in FIG. 22, in which a flow detector without the second exciting permanent magnets 4c and 4d is used, the magnetic flux density in the vicinity of an area, where the second exciting permanent magnets 4c and 4d are disposed, is increased. Accordingly, whichever part of the wire rope 1 has a damaged portion, a large magnetic field can be generated, and consequently, an amount of the leakage magnetic flux at the damaged portion of the wire rope can be increased.

As above-described, according to the present embodiment, a plurality of magnets are used, in a combined manner, as the exciting magnets, and are disposed such that the cross-sections of the respective magnets, when each magnet is cut along the plane perpendicular to the axial direction of the wire rope, embrace an outer circumference of the wire rope, and that the magnetic orientation on the cross-section of each magnet is oriented toward the wire rope. Accordingly, it is possible to obtain a larger amount of leakage magnetic flux at every point on the outer circumference of the wire rope 1, and also possible to obtain a signal having an SN ratio sufficient to be detected by the leakage magnetic flux detection section.

INDUSTRIAL APPLICABILITY

The present invention can be used widely as a wire rope flaw detector for detecting damage in a wire rope or a disconnection of a component wire.

The invention claimed is:

1. A wire rope flaw detector comprising:
   a magnetizer including a back yoke, and a pair of permanent magnets disposed on the back yoke such that polarities thereof are opposite to each other, and forming a main magnetic path in a predetermined segment in an axial direction of a wire rope; and
   a leakage magnetic flux detection section disposed in the predetermined segment in the axial direction, and detecting leakage magnetic flux generated from a damaged portion of the wire rope, wherein
   each of the permanent magnets (i) has a cross-section of a U-shape to embrace the wire rope when each permanent magnet is cut along a plane perpendicular to the axial direction of the wire rope, and (ii) has a magnetic orientation, on the cross-section of the permanent magnet, oriented toward the wire rope,
   a groove portion of each of the permanent magnets having the U-shaped cross section is magnetized to have a first magnetic pole, and
   an outer portion of each of the permanent magnets having the U-shaped cross-section is magnetized to have a second magnetic pole opposite the first magnetic pole.

2. The wire rope flaw detector according to claim 1, wherein each of the permanent magnets has a magnetic orientation, on the cross-section of the permanent magnet, oriented toward the center axis of the wire rope.

3. The wire rope flaw detector according to claim 1, wherein each of the permanent magnets includes two of U-shaped permanent magnets combined and disposed so as to have a cross-section embracing the entire circumference of the wire rope when the two combined magnets are cut along a plane perpendicular to the axial direction of the wire rope.

4. The wire rope flaw detector according to claim 1, wherein the leakage magnetic flux detection section includes a magnetic path member which is disposed so as to be magnetically insulated from the magnetizer and which causes leakage magnetic flux to detour around the wire rope, and a detection coil which is wound around the magnetic path member so as to detect the leakage magnetic flux.

* * * * *